United States Patent
Paltzer

(10) Patent No.: US 8,029,512 B2
(45) Date of Patent: Oct. 4, 2011

(54) SPINAL STABILIZATION DEVICE AND METHODS

(75) Inventor: Adam Paltzer, Marquette, MI (US)

(73) Assignee: Pioneer Surgical Technology, Marquette, MI (US)

( * ) Notice: Subject to any disclaimer, the term of this patent is extended or adjusted under 35 U.S.C. 154(b) by 1246 days.

(21) Appl. No.: 11/259,403

(22) Filed: Oct. 26, 2005

(65) Prior Publication Data

US 2006/0129238 A1 Jun. 15, 2006

Related U.S. Application Data

(60) Provisional application No. 60/622,029, filed on Oct. 26, 2004.

(51) Int. Cl.
*A61B 17/88* (2006.01)
(52) U.S. Cl. .................. 606/99; 606/914; 623/17.11
(58) Field of Classification Search .... 623/17.11–17.16; 606/99
See application file for complete search history.

(56) References Cited

U.S. PATENT DOCUMENTS

| | | |
|---|---|---|
| 1,816,446 A | 7/1931 | Stapf |
| 4,349,921 A | 9/1982 | Kuntz |
| 4,566,466 A | 1/1986 | Ripple et al. |
| 4,834,757 A | 5/1989 | Brantigan |
| 5,271,385 A | 12/1993 | Bailey |
| 5,443,514 A | 8/1995 | Steffee |
| 5,519,982 A | 5/1996 | Herber et al. |
| 5,525,363 A | 6/1996 | Herber et al. |
| 5,653,762 A | 8/1997 | Pisharodi |
| 5,716,415 A | 2/1998 | Steffee |
| 5,885,299 A * | 3/1999 | Winslow et al. ............... 606/99 |
| 5,888,224 A | 3/1999 | Beckers et al. |
| 5,893,890 A * | 4/1999 | Pisharodi .................. 623/17.16 |
| 6,004,326 A * | 12/1999 | Castro et al. ................. 606/99 |
| 6,042,582 A | 3/2000 | Ray |
| 6,063,088 A | 5/2000 | Winslow |
| 6,080,155 A | 6/2000 | Michelson |
| 6,080,158 A * | 6/2000 | Lin ............................. 606/247 |
| 6,096,038 A | 8/2000 | Michelson |
| 6,113,639 A * | 9/2000 | Ray et al. .................. 623/17.16 |
| RE37,005 E * | 12/2000 | Michelson et al. ............ 606/99 |
| 6,224,607 B1 * | 5/2001 | Michelson ..................... 606/96 |

(Continued)

FOREIGN PATENT DOCUMENTS

CA 1146301 5/1983

(Continued)

*Primary Examiner* — Eduardo C Robert
*Assistant Examiner* — Jerry Cumberledge
(74) *Attorney, Agent, or Firm* — Fitch, Even, Tabin & Flannery

(57) ABSTRACT

Devices and methods for immobilizing adjacent vertebrae are disclosed including the utilization of one or more implants inserted between adjacent vertebrae and having protrusions thereon for substantially fixedly securing with the vertebrae. In one form, an implant may be inserted in a first orientation and then rotated to a second orientation having a larger profile. A second implant may also be inserted in the same vertebral space in the same manner. A trial spacer may be used to determine the proper implant size. In another form, an implant may be inserted already in the fusion orientation. The implants and trial spacer, as well as a spreader and/or a scraper for preparing the intervertebral space, may be inserted in the vertebral space with the same insertion tool. The inserter tool may include a threaded member for attachment with the implants or other devices.

11 Claims, 19 Drawing Sheets

U.S. PATENT DOCUMENTS

| | | |
|---|---|---|
| 6,270,498 B1 | 8/2001 | Michelson |
| 6,290,724 B1 | 9/2001 | Marino |
| 6,309,400 B2 * | 10/2001 | Beaupre .................. 606/169 |
| 6,579,318 B2 | 6/2003 | Varga et al. |
| 6,719,794 B2 * | 4/2004 | Gerber et al. ............ 623/17.11 |
| 6,770,074 B2 | 8/2004 | Michelson |
| 6,835,206 B2 * | 12/2004 | Jackson ................. 623/17.11 |
| 6,942,670 B2 * | 9/2005 | Heldreth et al. ............ 606/102 |
| 7,125,425 B2 * | 10/2006 | Foley et al. ............ 623/17.16 |
| 2002/0177897 A1 * | 11/2002 | Michelson ............... 623/17.11 |
| 2003/0023306 A1 * | 1/2003 | Liu et al. ................. 623/17.11 |
| 2003/0130737 A1 * | 7/2003 | McGahan et al. ......... 623/17.11 |
| 2003/0139816 A1 * | 7/2003 | Michelson ............... 623/17.11 |
| 2003/0195629 A1 | 10/2003 | Pafford et al. |
| 2004/0093083 A1 * | 5/2004 | Branch et al. ............ 623/17.11 |
| 2004/0133207 A1 * | 7/2004 | Abdou ..................... 606/73 |
| 2004/0162616 A1 * | 8/2004 | Simonton et al. .......... 623/17.11 |
| 2004/0167628 A1 * | 8/2004 | Foley .................... 623/17.16 |
| 2004/0176853 A1 * | 9/2004 | Sennett et al. ............ 623/17.16 |
| 2005/0004672 A1 | 1/2005 | Pafford et al. |
| 2005/0182416 A1 * | 8/2005 | Lim et al. ................. 606/90 |
| 2005/0278026 A1 * | 12/2005 | Gordon et al. ............ 623/17.11 |
| 2006/0095043 A1 * | 5/2006 | Martz et al. ............... 606/90 |
| 2007/0100212 A1 | 5/2007 | Pimenta et al. |

FOREIGN PATENT DOCUMENTS

| | | |
|---|---|---|
| EP | 0042271 | 12/1981 |
| EP | 0834295 | 4/1998 |
| EP | 1346695 | 9/2003 |
| FR | 2703580 | 10/1994 |
| FR | 2841124 A1 * | 12/2003 |
| WO | 9000037 | 1/1990 |
| WO | 9428824 | 12/1994 |
| WO | 2004000177 | 12/2003 |

* cited by examiner

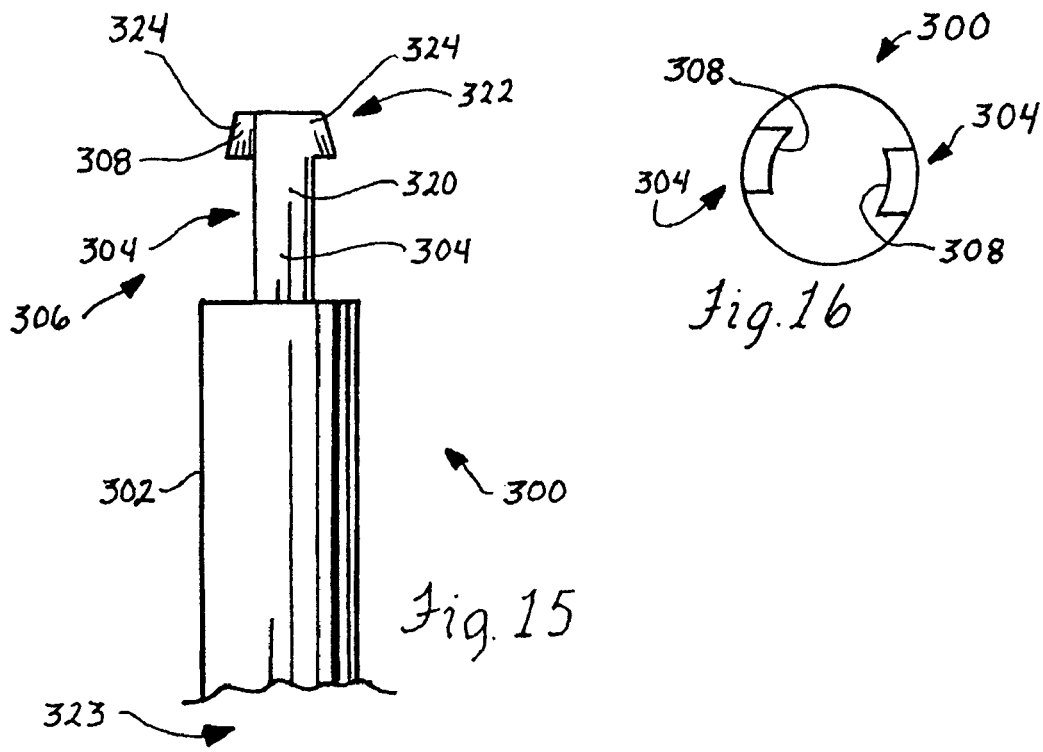
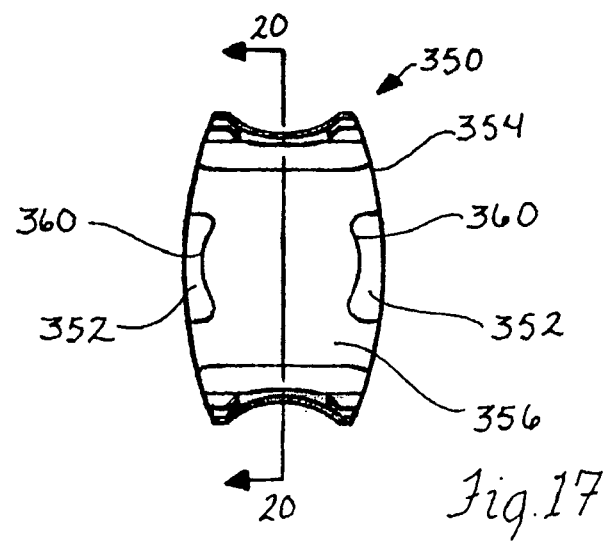

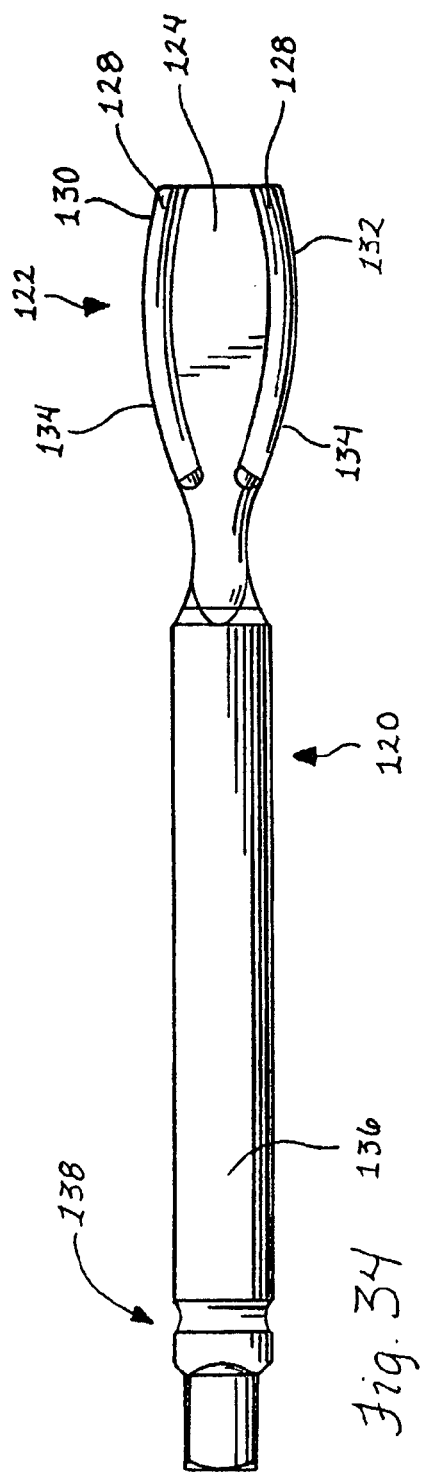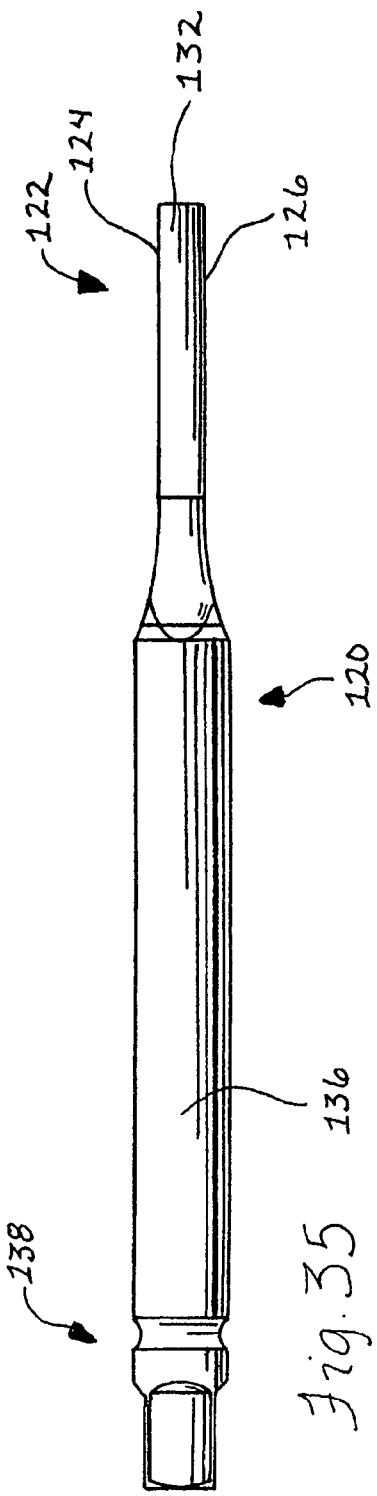

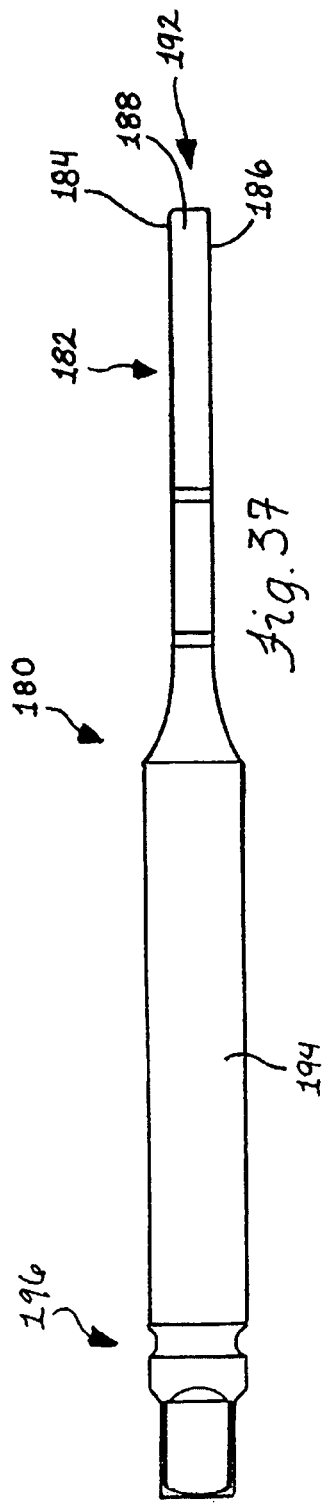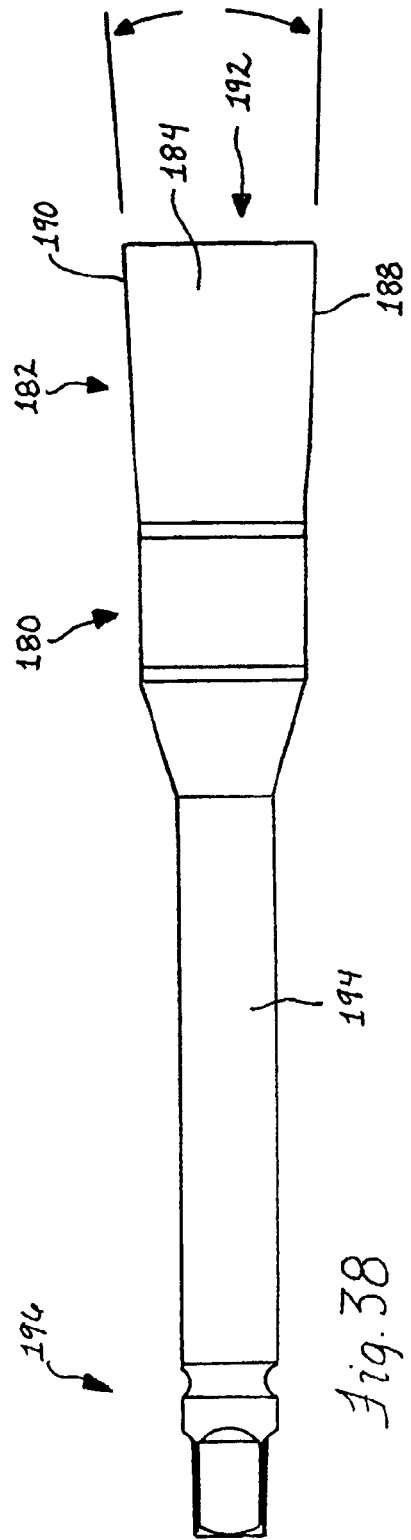

SPINAL STABILIZATION DEVICE AND METHODS

CROSS-REFERENCE TO RELATED APPLICATION(S)

This application claims priority to U.S. Provisional Application Ser. No. 60/622,029, filed Oct. 26, 2004, and titled "Spinal Stabilization Device and Methods," the entirety of which is incorporated herein by reference.

FIELD OF THE INVENTION

The invention relates to spinal stabilization devices and methods and, in particular, to devices for implantation in a vertebral space between adjacent vertebrae for immobilization and fusion of the vertebrae and methods for implantation of such devices and insertion of related components into the vertebral space.

BACKGROUND OF THE INVENTION

Spinal damage, disease, or deformity are serious and often painful conditions that may become life-threatening conditions. Some conditions impinge on the spine and lead to pain, such as disc degeneration or tumors. Others conditions involve abnormalities, such as scoliosis or spinal stenosis, where a person's spine is more susceptible to injury or damage.

Pain is a common result from disease in, damage to, or degeneration of spinal members such as vertebrae and discs, most often from bone or tissue surrounding the spine cord impinging on the spinal cord itself. If the spinal cord is damaged, either directly or by the inability of the damaged vertebrae to protect the spinal cord, the communication between the brain and organs or limbs may be lost, resulting in organ failure or paralysis. Such conditions, if not properly managed, can lead to long-term pain, other complications, and ever-diminishing quality of life.

Many injuries to the spinal cord are not necessarily as a result of the principal injury itself. For example, an injury sustained in an accident may be one or more vertebrae being shattered or spinal discs herniated. Other times, a disc may degenerate from a minor injury sustained many years prior, or simply from the age of the body. These injuries do not necessarily impact the spinal cord in a permanent manner, other than leading to pain. The vertebral fragments or damaged nucleus will likely impinge on the spinal cord, causing pain, numbness, or reduced motor capabilities in the limbs. Removal of the impingement, and reduced swelling from the damaged or diseased tissue including the spinal cord, often promotes healing and the return of normal nervous system functioning. However, in the absence of proper medical care, a person's health may continue to degenerate, and the spine is often more susceptible to injury. In addition, the spinal cord may become permanently damaged.

The spine provides a number of specific physiological functions. The spine enables a torso to be rotated, to bend laterally, and to flex in anterior-posterior directions, or a combination of these. In addition, the spine supports the weight of the torso and the limbs attached thereto, including the head. The spine supports the body under stress or shock resulting from a person's activities such as weight-lifting, contact sports, or inadvertent accidents, though with limits. A head-on collision, such as from playing football, may result in an injured or herniated spinal disc where a portion of the spinal annulus is damaged and leaks. In addition, disease or abnormalities may be present, such as scoliosis where symptoms manifest themselves over an extended period of time. In any event, degeneration over time often results in a loss of disc support, and treatment is required to reduce or eliminate pain, such as immobilization to strengthen a portion of the spine.

Immobilization of a spinal column is often prescribed for treating a spinal condition. Swelling or pressure on the spinal column can create temporary problems that may become permanent if not properly addressed. Similarly, removal of a diseased portion of the spine or surrounding tissue may make the spine vulnerable to damage. In the event of a degenerative condition, treatment is required at some point to eliminate pain or to reduce the likelihood of a catastrophic failure. A number of approaches have been developed for this immobilization.

The type of condition often suggests the technique employed for treatment. For instance, damage to a nucleus may be minimal, which invites a treatment that attempts to repair the nucleus. A fractured vertebra would likely be braced in some way, such as with a bone plate, to immobilize the vertebral segments to encourage the fracture to heal.

In some cases, a manner of treating spinal conditions is known as spinal fusion surgery. Two or more vertebrae may be fused or immobilized relative to each other to maintain the intervertebral distance, to maintain or replicate the integrity of the spine for support, and to prevent rotation or flexion between the affected vertebrae. Though such a prescription results in some loss of movement and flexibility to the spine, it is seen as a suitable manner for protecting the spine and spinal cord from injury and reducing pain from compression on the spinal cord. Moreover, the other, unaffected spinal portions may compensate to provide most of the normal movement.

Accordingly, there has been a need for improved spinal fusion systems and for improved methods for performing spinal fusion surgery.

BRIEF DESCRIPTION OF THE DRAWINGS

FIG. 15 is a fragmentary side elevational view of the engagement end portion of the inserter tool of FIG. 14 showing enlarged grip heads at the ends of the prongs;

FIG. 16 is an end elevational view of the engagement end portion of the inserter tool of FIG. 14 showing the spacing of the prongs about a shaft of the insertion tool;

FIG. 17 is a rear end elevational view of a rear connection end portion of the VBR device of FIG. 13 showing an arcuate configuration for the receiver channels;

FIG. 34 is a side elevational view of a scraping tool showing a blade scraping head thereof;

FIG. 35 is a side elevational view of the scraping tool rotated ninety degrees from the FIG. 34 position showing a narrow width of the scraping head;

FIG. 37 is a side elevational view of a spreading tool showing a distraction head having a thin width for ease of insertion between adjacent vertebrae;

FIG. 38 is a side elevational view of the spreading tool rotated ninety degrees from the FIG. 37 position to show the tool height for distracting the adjacent vertebrae;

DESCRIPTION OF THE PREFERRED EMBODIMENTS

Figure 1:
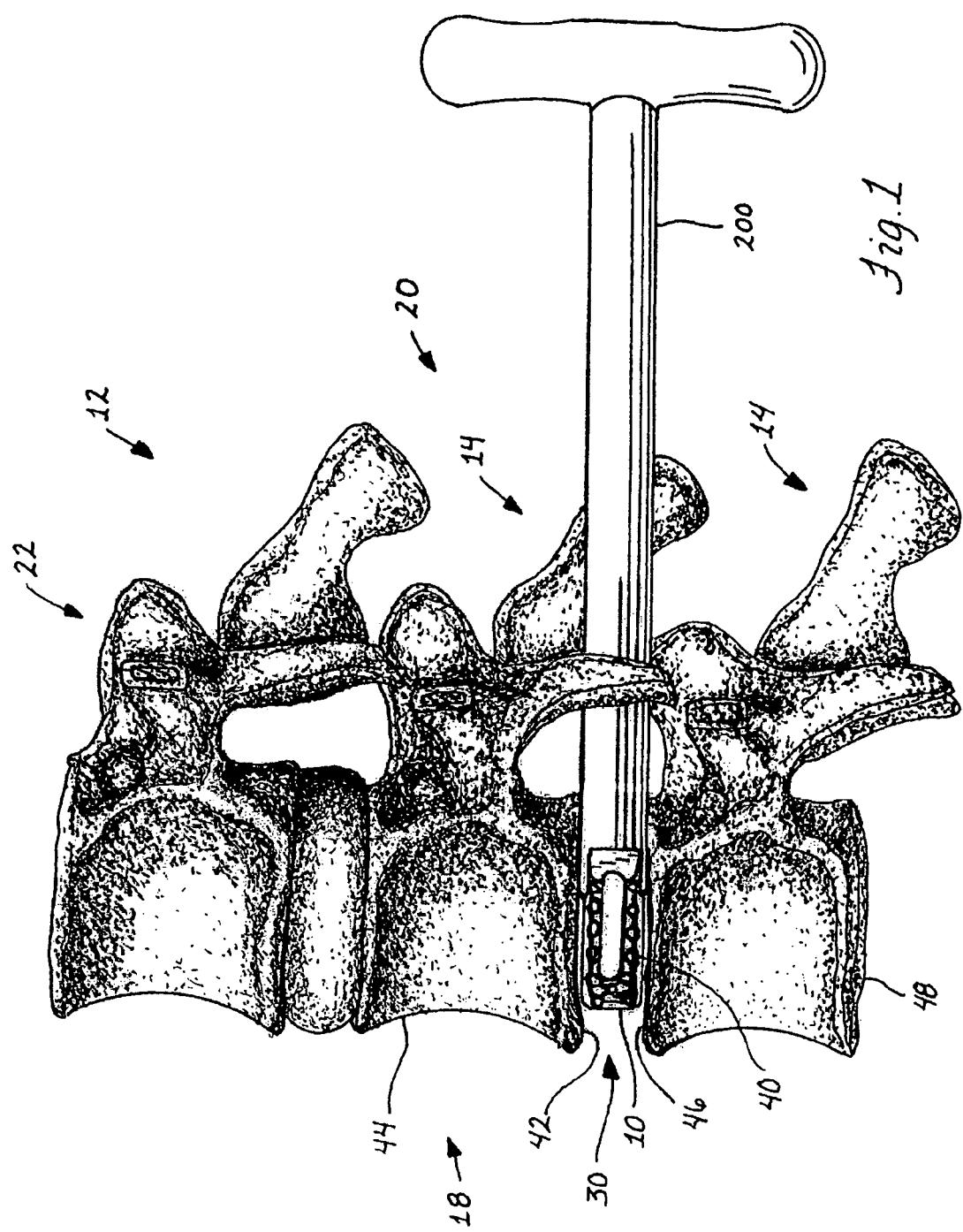
FIG. 1 is a representational view of a vertebral body replacement (VBR) device in accordance with the present invention showing the VBR device connected to an insertion tool in an insertion orientation and inserted between adjacent vertebrae.
Figure 2:
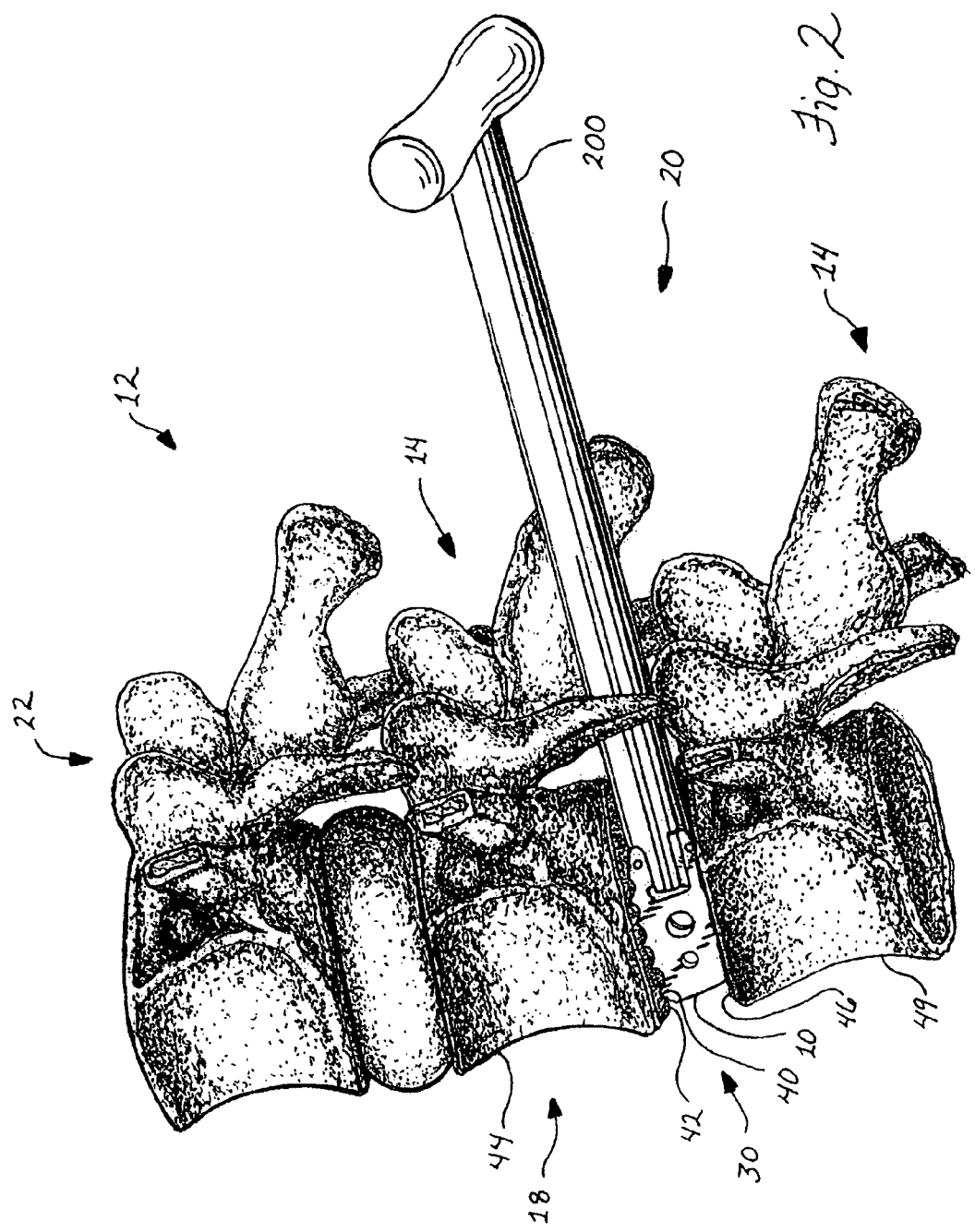
FIG. 2 is a representational view of the VBR device and tool of FIG. 1 showing the VBR device turned to an implantation orientation by the tool.

Referring initially to FIGS. 1 and 2, a vertebral body replacement device or implant 10 for spinal fusion surgery is represented as being inserted within a spinal column 12. The spinal column includes a series of vertebrae 14 and spinal discs 16 located between adjacent vertebrae 14. The spinal column 12 has an anterior side 18 and a posterior side 20 wherein the vertebrae 14 include a portion 22 on the posterior side 20 in which the spinal cord (not shown) is located.

In FIGS. 1 and 2, the implant 10 is shown being inserted from a posterior side 20 into an intervertebral space 30. Through the lumbar region of the spine 12, access to the intervertebral space 30 from the posterior side 20 avoids needing to go through the abdomen, which would require a general surgeon. In the cervical region (not shown) of the spine 12, it is preferred to access the spine 12 from the anterior side 18, principally due to the curvature of the cervical vertebrae. An implant 500 for use in the cervical region is presented in FIGS. 22-26 and accompanying text.

Figure 3:
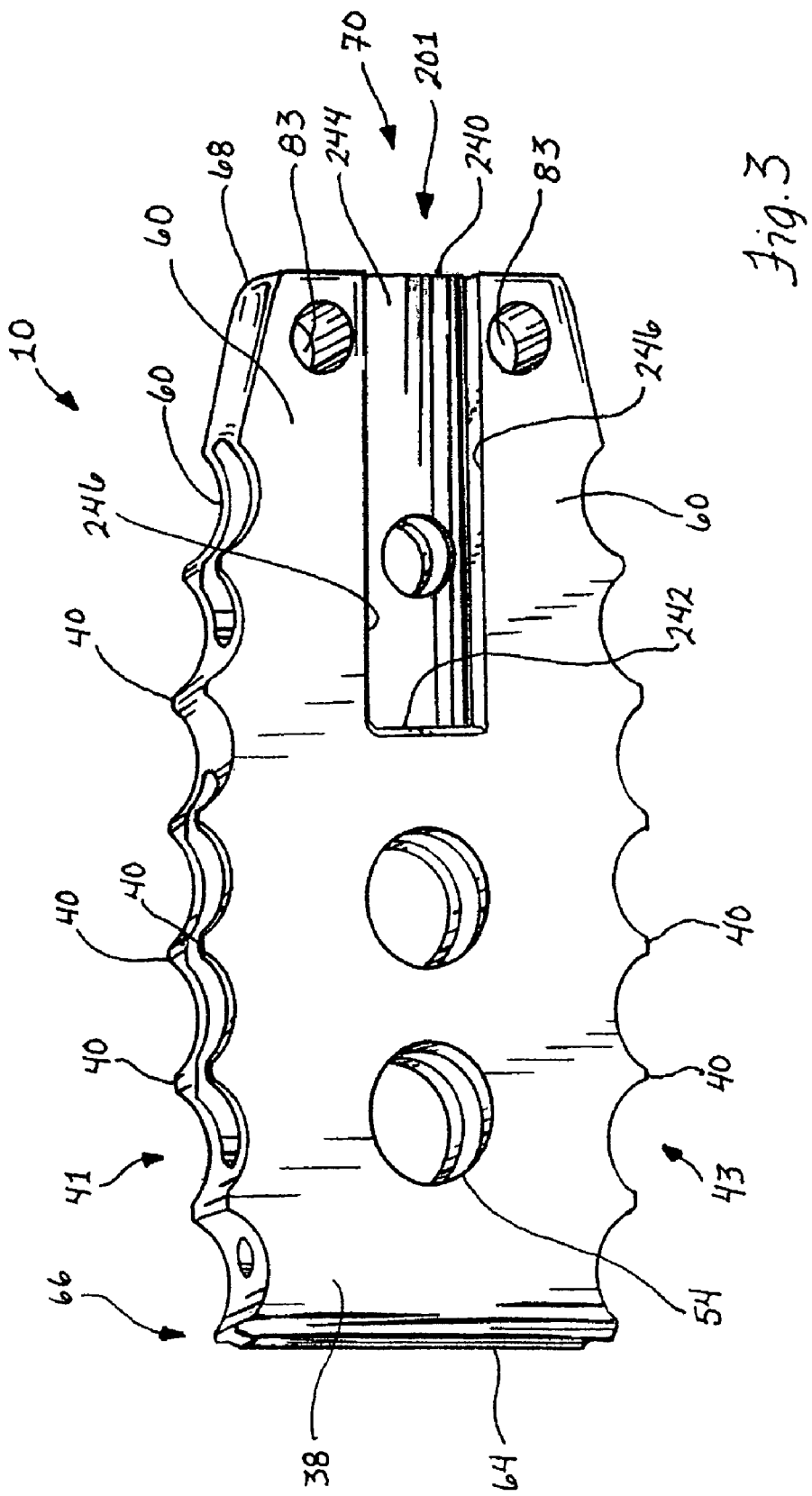
FIG. 3 is a perspective view of the VBR device showing an elongated body of the device with one of a pair of receiver channels on either side of the body for connecting to the insertion tool.

The implant 10 includes a body 38 having gripping surfaces 41, 43 (see FIG. 3) located on a predetermined exterior or outer portion of the implant body 38 so that, with the VBR device shifted to its implantation orientation, the gripping surfaces 41, 43 contact a superior endplate 42 located on the superior vertebra 44 and an inferior endplate 46 located on the inferior vertebra 48. The implant 10 has an insertion orientation, represented in FIG. 1, such that the gripping surfaces 41, 43 are not in gripping engagement with the respective endplates. More particularly, in the insertion orientation the gripping surfaces 41, 43 will face in opposite lateral directions transverse to an axis X (see FIG. 1) of the spinal column 12. Once in the desired position in the intervertebral space 30, the implant 10 is rotated to a fusion or implantation orientation so that the gripping surfaces 41, 43 are securely engaged with the endplates 42 46. The fusion orientation substantially immobilizes the adjacent vertebrae 14 relative to each other and with the implant 10.

By immobilizing the vertebrae 14 and implant 10, fusion of the vertebrae 14 with each other and with the generally permanent implant 10 is promoted. As will be discussed in greater detail below, the implant 10 is preferably filled with bone graft material and has a generally open structure for allowing fluid flow and bone ingrowth through the implant 10. While securement of the implant 10 in the intervertebral space 30 substantially immobilizes the implant 10 and the vertebrae 14, bone ingrowth beneficially allows the adjacent vertebrae 14 to become a single, generally rigid structure with increased strength for supporting the spinal column 12 and the rest of the patient's body, such as their torso.

For a posterior approach to the spine, the portion 22 for the spinal cord is directly in line with the posterior side 20. Therefore, the direction of approach is actually slightly offset from the anterior-posterior direction. The vertebrae 14 in the lumbar region tend to be relatively wide in comparison to the other regions of the spine, and it is preferred to provide support across the full widthwise extent of the endplates 42, 46.

Due to the constraints rendered by the posterior approach and avoiding the spinal cord portion 22, it is therefore preferable to secure a pair of the present implants 10 in the lumbar region intervertebral space 30. A first implant 10 is inserted from the posterior side 20 and either to the right or left of the spinal cord portion 22. A second implant 10 is then inserted from the other side of the spinal cord portion 22, again from the posterior side 20.

Figure 7:
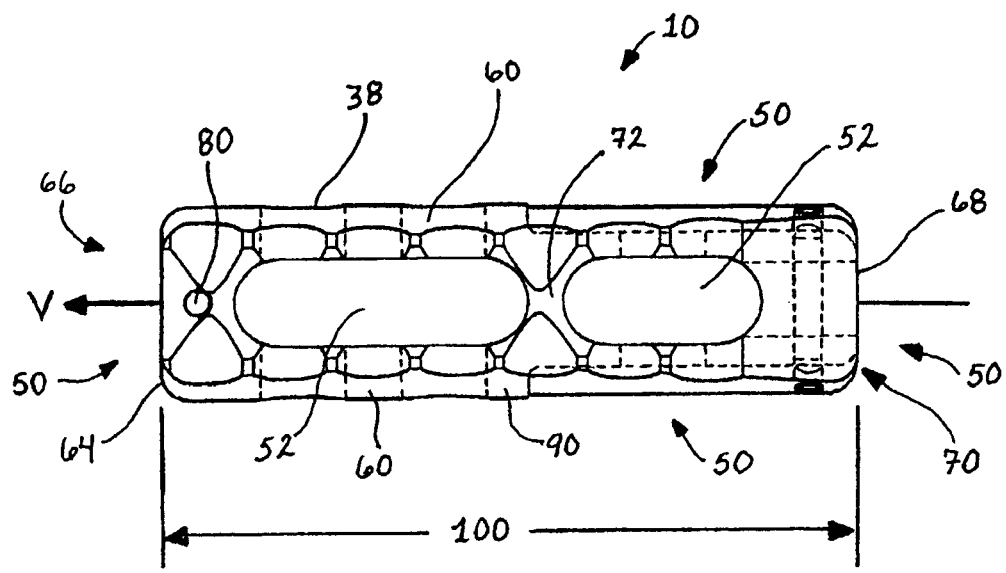
FIG. 7 is a plan view of the VBR device showing forward and rearward inner cavities for receiving material to promote bone ingrowth and a front through aperture for a marker member.
Figure 8:
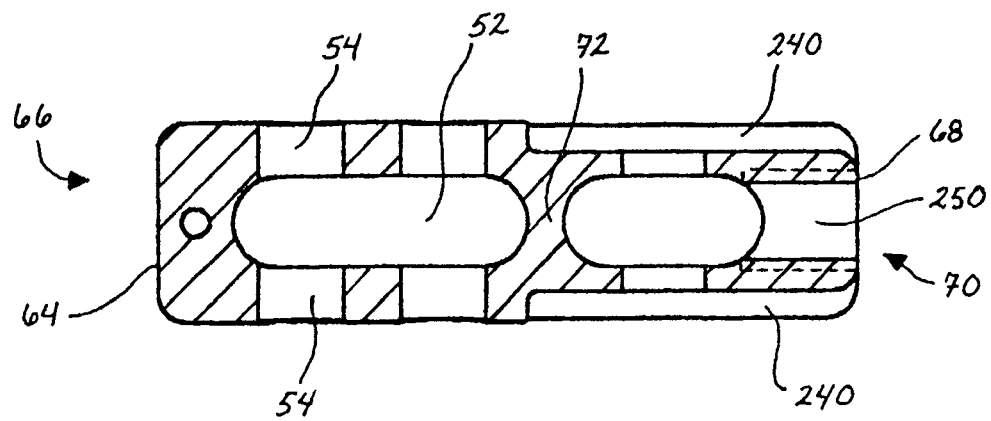
FIG. 8 is a cross-sectional view taken along line 8-8 of FIG. 4 showing communication of the inner cavities with the transverse through bores of the VBR device.
Figure 9:
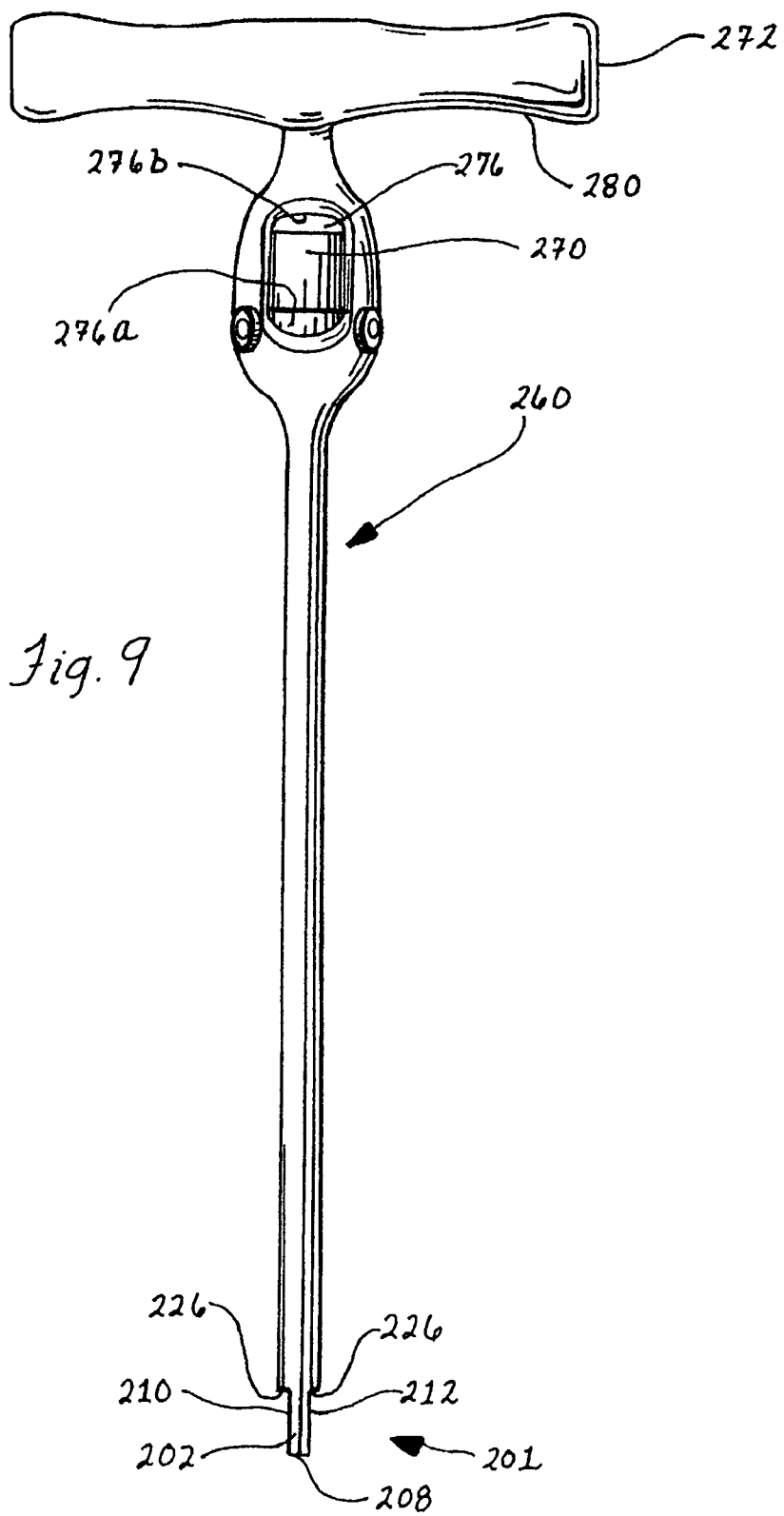
FIG. 9 is a perspective view of the inserter tool showing a handle at one end and an opposite VBR device engagement end portion thereof.
Figure 10:
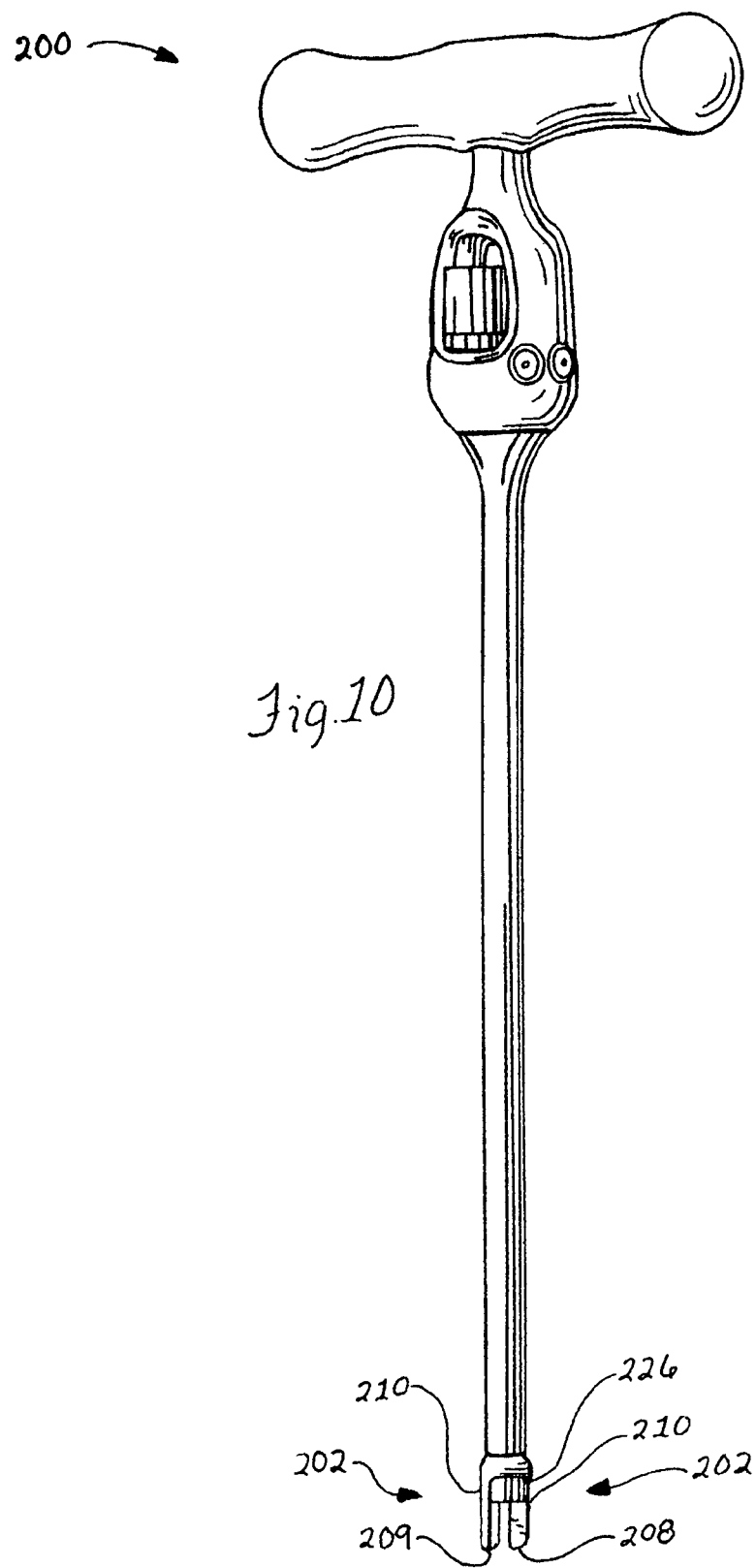
FIG. 10 is a perspective view of the inserter tool showing a pair of spaced prongs of the engagement end portion.
Figure 11:
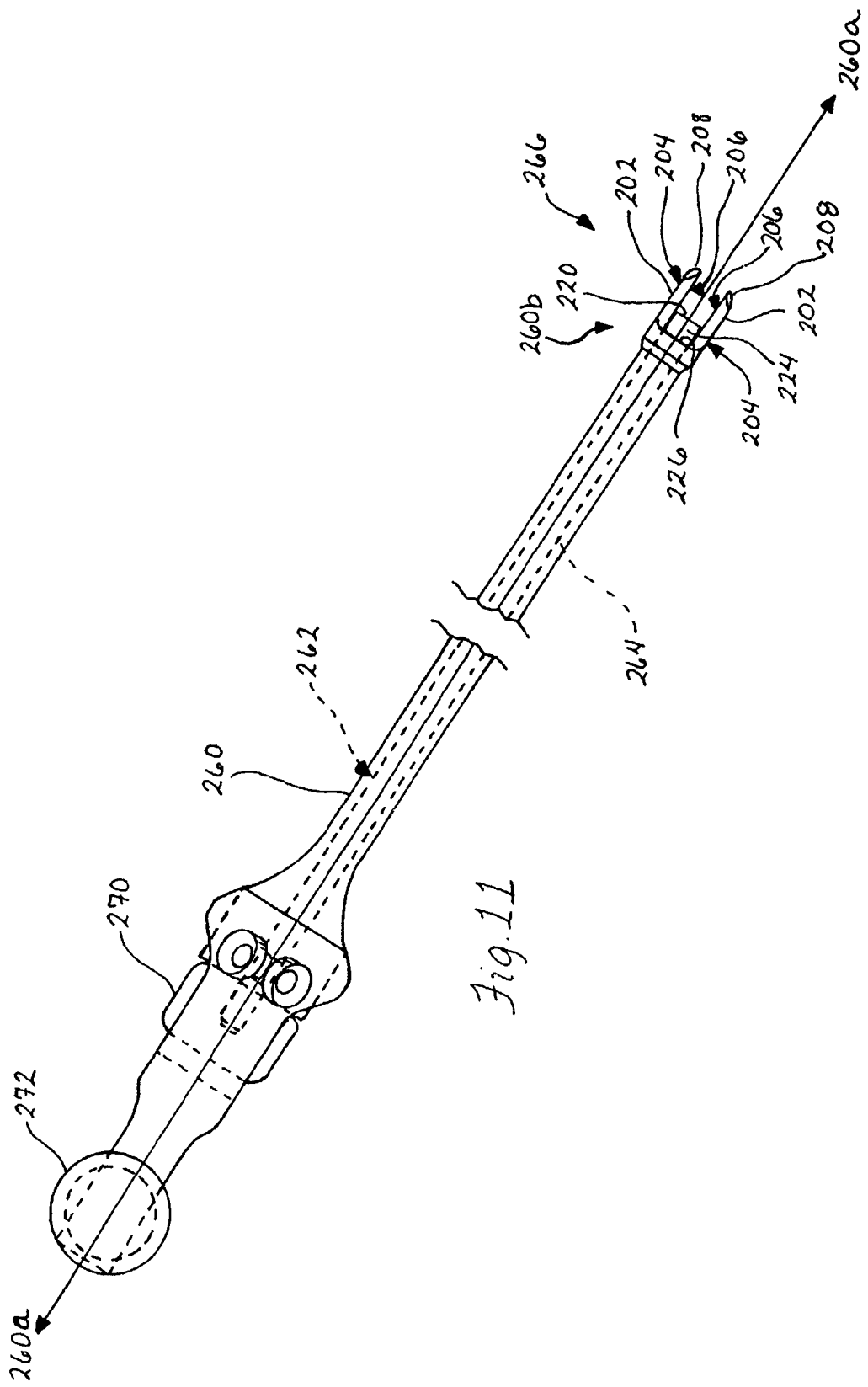
FIG. 11 is a side elevational view of the inserter tool showing an insertion member advanced to an engagement position.
Figure 12:
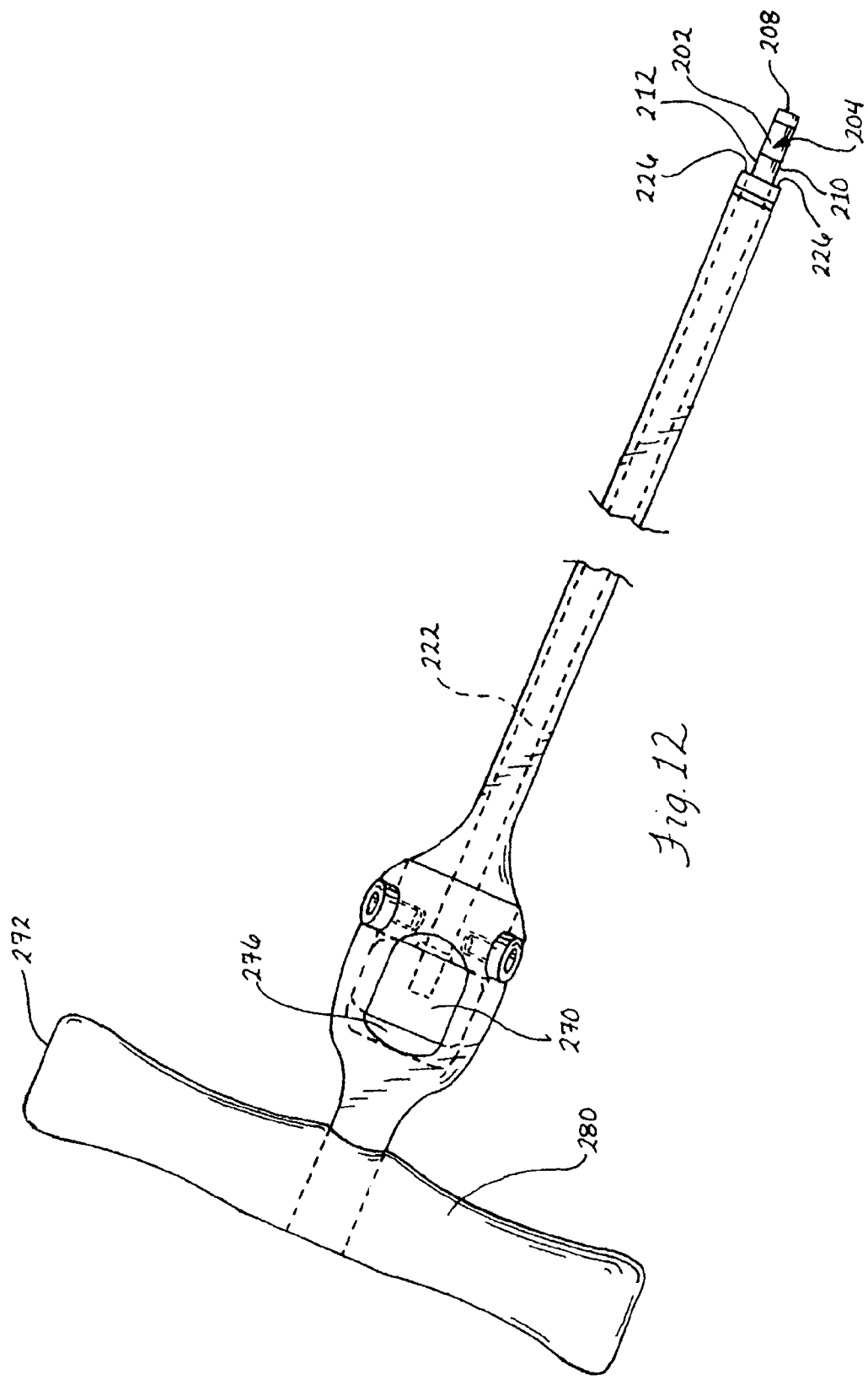
FIG. 12 is side elevational view of the inserter showing a rotary knob actuator for advancing and retracting the insertion member.
Figure 13:
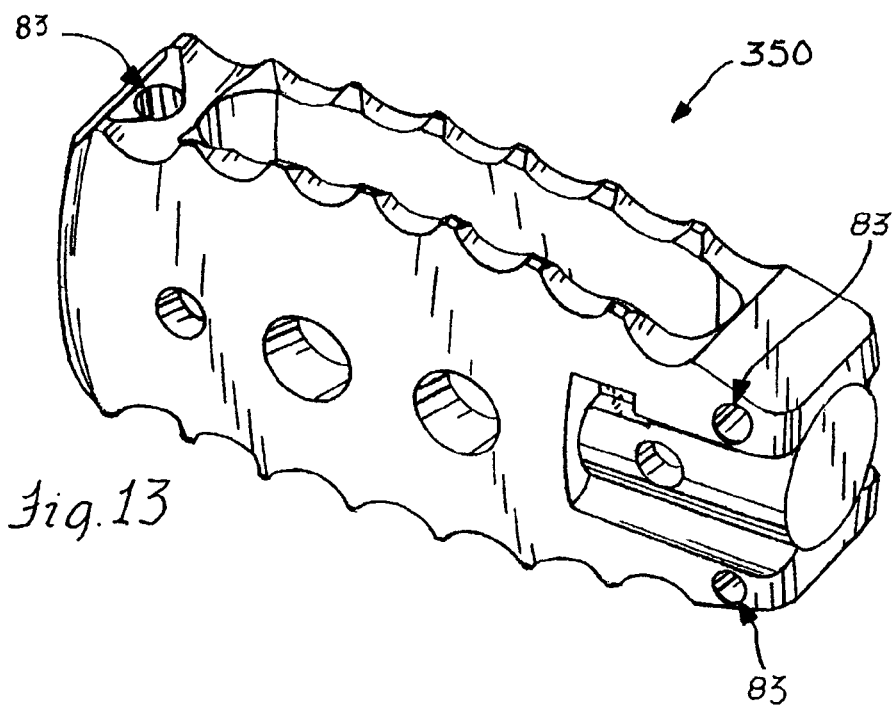
FIG. 13 is a perspective view of a further embodiment of the VBR device showing the body having alternative tool connection structure.
Figure 14:
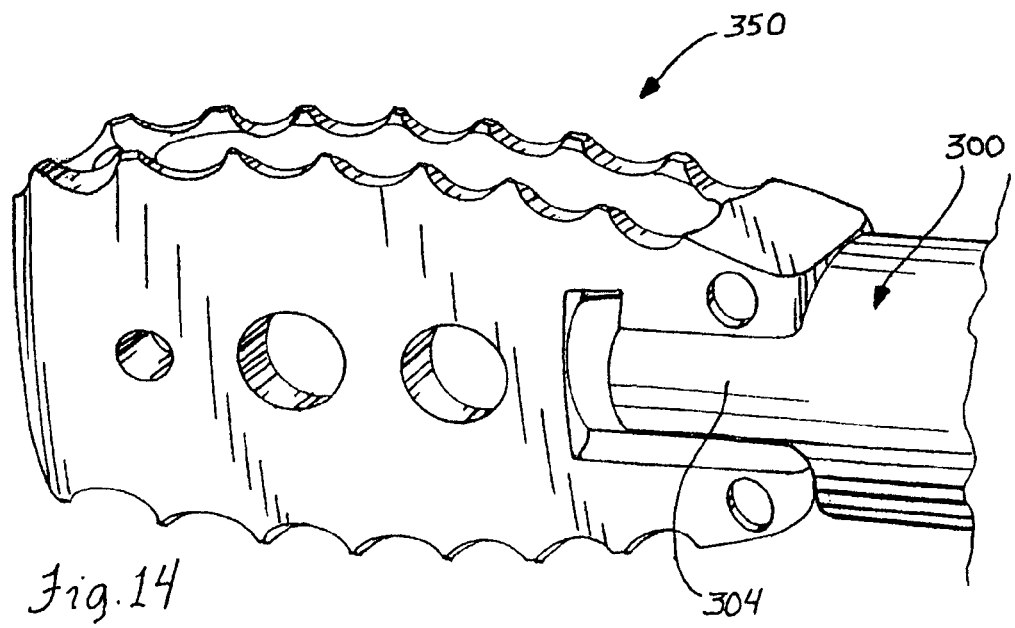
FIG. 14 is a perspective view of the VBR device of FIG. 13 showing an engagement end portion of an inserter tool connected to the VBR device.

As is best seen in FIG. 7, the body of the implant 10 generally has a box shape configuration including a plurality of walls 50, though sidewalls 60 have an outward arcuate or barrel-shaped profile. Bone ingrowth with and around the implant 10 benefits from the provision of bone graft material and fluid flow. Toward this end, the body walls 50 substantially define one or more internal cavities 52 into which bone graft material is packed prior to insertion in the intervertebral space 30. The implant body 38 further includes holes or throughbores 54 extending transversely through the implant body 38 and, more specifically, through sidewalls 60 thereof. The open structure of the implant 10 allows fluid to flow throughout the intervertebral space 30, which is also packed with bone graft material, and allows developing bone to spread throughout the intervertebral space 30 including about, through, and within the implant body 38 fixed in the space 30.

Figure 6:
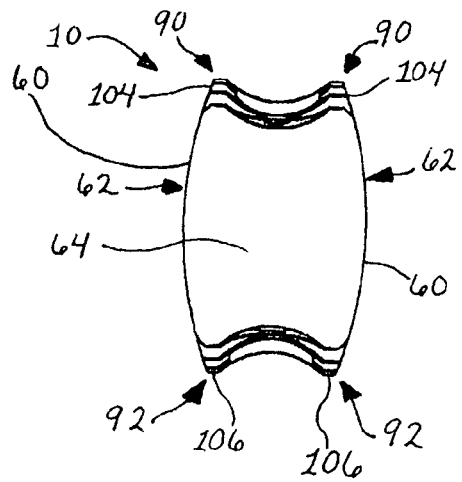
FIG. 6 is a front end elevational view of a front insertion end of the VBR device body for being inserted between adjacent vertebrae.

As noted, the implant 10 is inserted into the intervertebral space 30 in the insertion orientation, and is then rotated about its longitudinal axis V to the fusion orientation. The implant 10 is inserted with the sidewalls 60 facing or contacting the corresponding endplates 42, 46. To facilitate rotation from the insertion orientation to the fusion orientation, the sidewalls 60 are provided with an outer surface 62 that is arcuately profiled about the implant axis, as can best be seen in FIG. 6. This allows the initial rotation of the implant 10 to follow the curve of the outer surface 62, thus making it easier to begin the rotation.

A number of features are present in the implant 10 to provide structural integrity. The implant 10 has a front wall 64 formed at an insertion or leading end 66, and a rear wall 68 formed at a connection end 70, the front wall 64 and rear wall 68 spanning between the laterally spaced sidewalls 60. An additional transverse wall or web 72 can be provided for strength purposes. However, the presence of the web 72 reduces the volume of the cavity 52 and, thus, the amount of bone graft material that may be placed therein.

Figure 21:
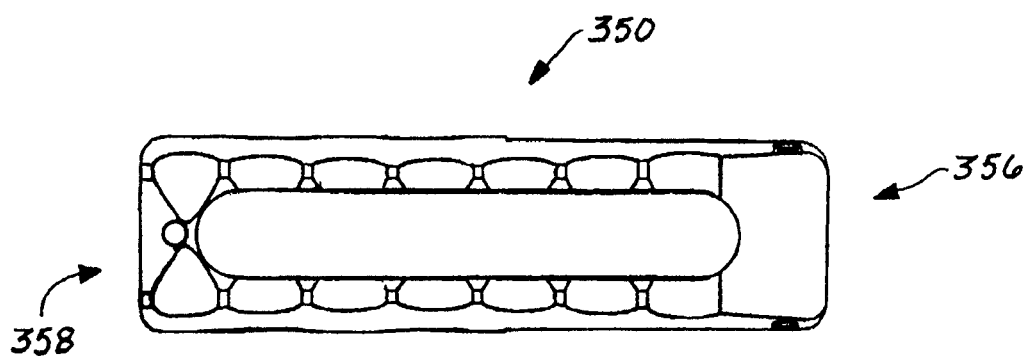
FIG. 21 is a plan view of the VBR device of FIG. 13 showing a single inner cavity for receiving material to promote bone ingrowth.
Figure 22:
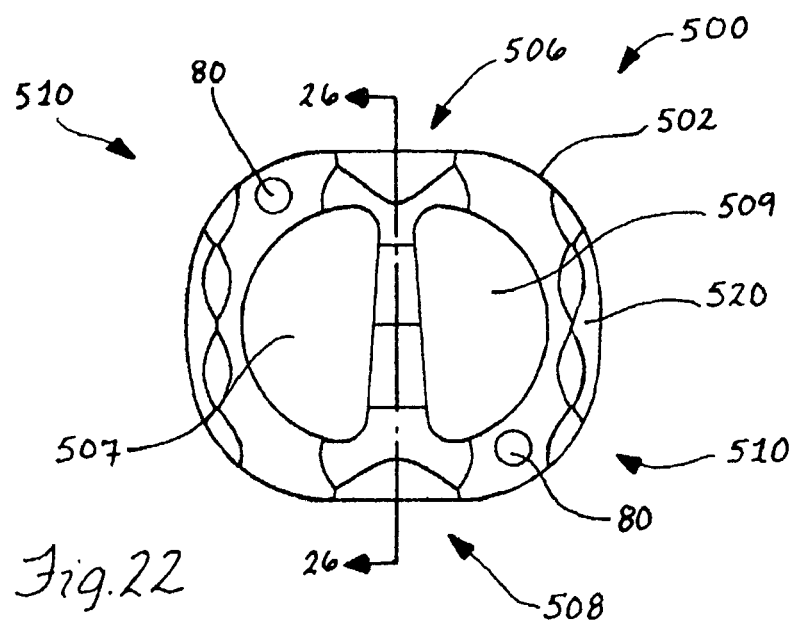
FIG. 22 is a plan view of a further form of a VBR device showing a generally annular outer wall and an inner web wall to form a pair of inner cavities for receiving material to promote bone ingrowth.
Figure 23:
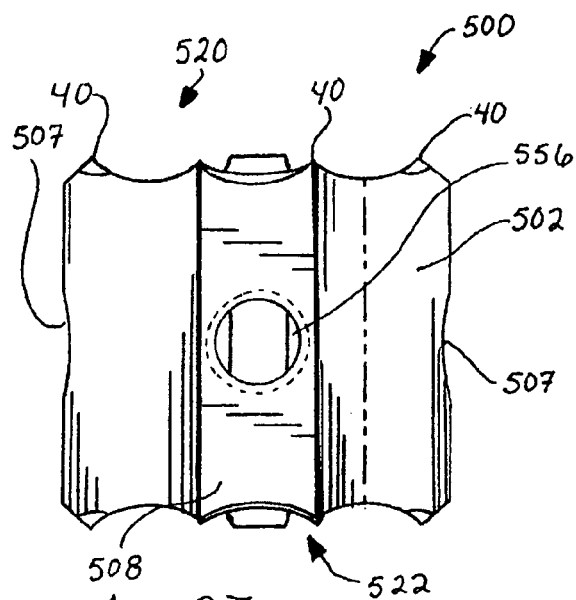
FIG. 23 is a front elevational view of the VBR device of FIG. 22 showing a connection end portion including a connection opening.
Figure 24:
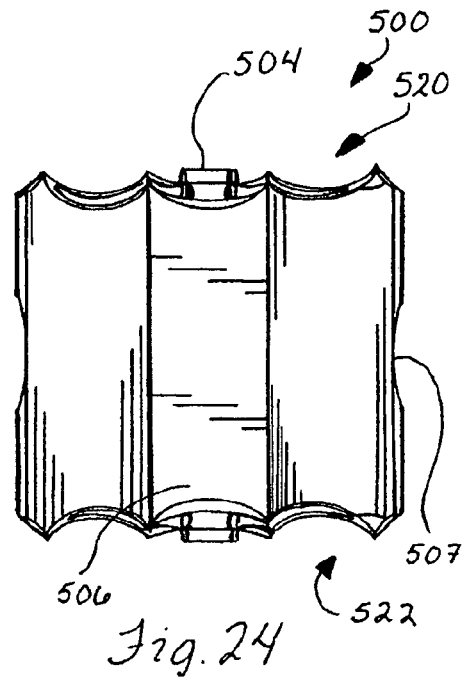
FIG. 24 is rear elevational view of the VBR device of FIG. 22 showing an insertion end thereof.
Figure 25:
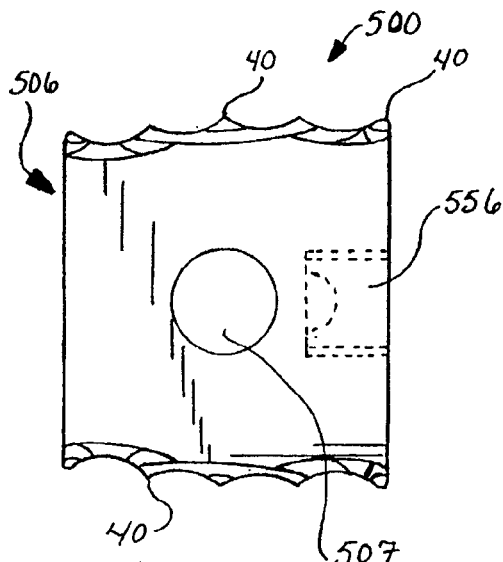
FIG. 25 is a side elevational view of the VBR device of FIG. 22 showing a transverse throughbore for permitting bone ingrowth in the body.
Figure 26:
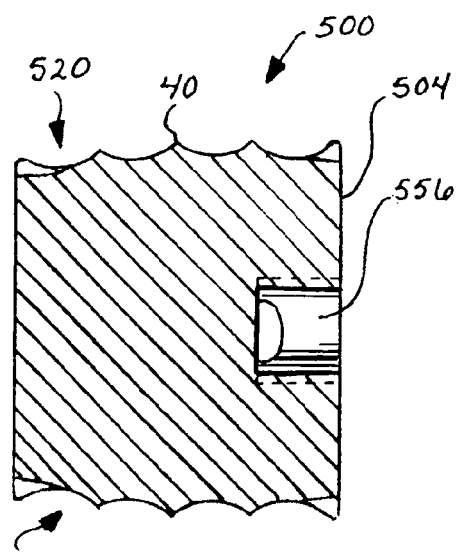
FIG. 26 is a cross-sectional view of the VBR device taken through the line 26-26 of FIG. 22 showing the connection opening and upper and lower undulating surfaces of the web wall for engaging adjacent vertebrae.

For just about every patient, their spinal geometry and size is unique. Accordingly, a variety of sizes of the implant 10 are provided. It is believed that the presence of the web 72 is not necessary for larger sizes of the implant 10 to maintain strength and integrity. Accordingly, it is preferred that smaller-sized implants 10 utilize the web 72, while it is omitted in larger implants 10, as can be seen for implant 350 in FIG. 21.

The implant 10 may also include radiographic markers in the form of rod-like members 80, 81, as will be discussed more fully below, received in marker apertures 83 and improving the strength properties of the implant 10. The implant 10 may be made of any biocompatible material, though a polymer is preferred, particularly PEEK. The marker members 80, 81, on the other hand, are preferably titanium or stainless steel, which is considerable stronger than the PEEK. To utilize this fact, the front wall 64 includes a marker member 80 generally positioned to extend between the gripping surfaces 41, 43, or vertically with the implant device 10 in the implantation orientation thereof, thus improving the compression capabilities of the implant body 38 at the front wall 64 and thus the insertion end 66.

Additionally, radiographic markers 81 may be utilized to improve the strength of the implant body 38 to take the stress of rotation from the insertion orientation to the fusion orientation. As will be discussed in greater detail below, an insertion tool 200 is utilized for holding, inserting, positioning, and rotating the implant 10. To accomplish these, the inserter 200 is removably attached to the sidewalls 60 and to the rear wall 68.

Figure 4:
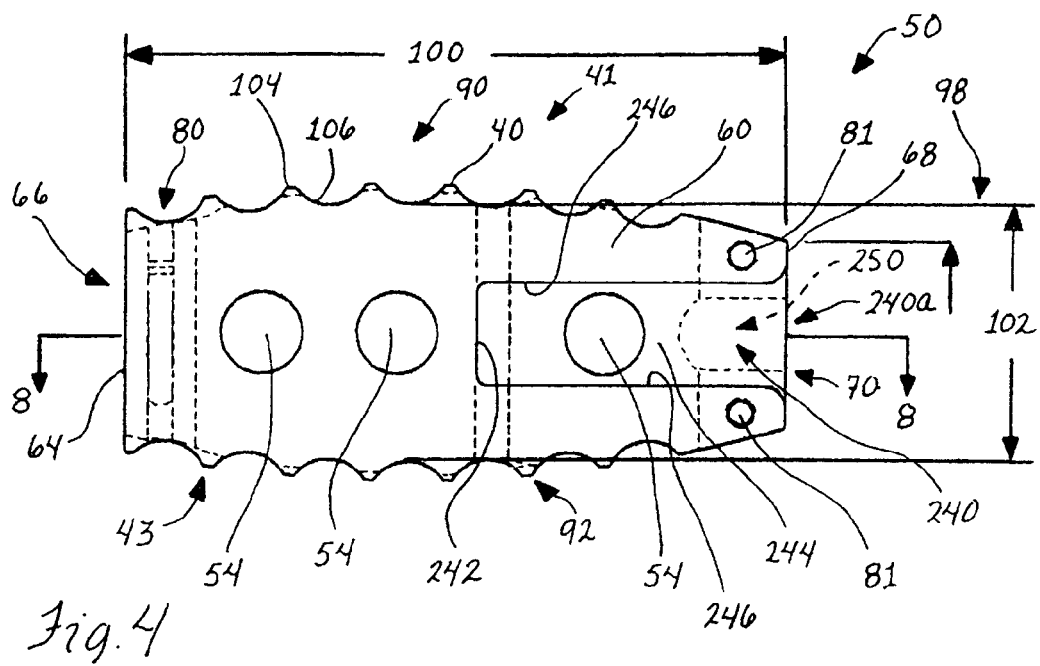
FIG. 4 is a side elevational view of the VBR device showing transverse through bores for permitting bone ingrowth into the body.
Figure 5:
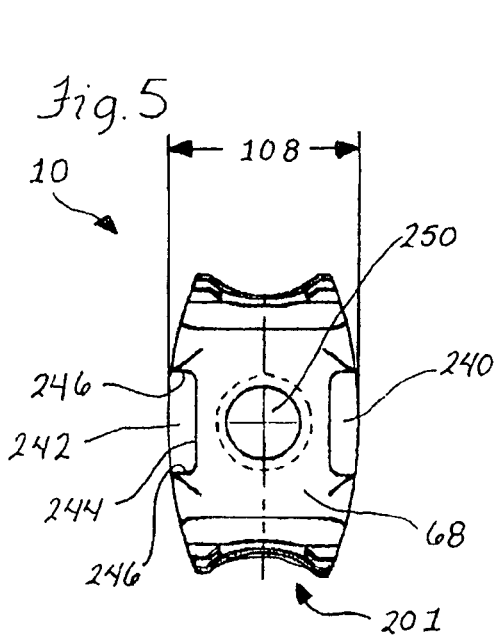
FIG. 5 is a rear end elevational view of a rear connection end portion of the VBR device showing a connection opening between the receiver channels for connecting to the insertion tool.

Much of the stress of rotation is transmitted through the inserter 200 to the sidewalls 60. Accordingly, two radiographic markers in the form of rod members 81 oriented to extend laterally or generally horizontal in the fusion orientation are included with the implant 10, one each above and below the region of the sidewalls 60 to which the inserter 200 is secured and spanning through the rear wall 68. With reference to FIGS. 4 and 5, the marker members 81 can be seen extending laterally above and below the connection opening 250 and above and below rear open ends 240a of the receiver channels 240. During rotation then, the horizontal or transversely oriented marker members 81 provide additional strength and rigidity to the implant 10 in close proximity to the engagement region between the implant body 38 and the inserter tool 200.

The radiographic markers also serve to provide a surgeon a clear view of the position and orientation of the implant 10. When the implant 10 is properly in the fusion orientation, the markers 80, 81 form an "I" shape. However, when the implant 10 is not in the fusion orientation, the markers 80, 81 form an "H" shape.

As has been mentioned, the implant 10 includes gripping surfaces 41, 43 for permanent, substantially fixed securement with the endplates 42, 46. As illustrated, the gripping surfaces 41, 43 have an undulating configuration extending axially so that there are peaks 104 and troughs or valleys 106 along the surfaces 41, 43 to define a plurality of axially spaced protrusions 40 along the gripping surfaces 41, 43. The protrusions 40 may be located on upper and lower surfaces 90, 92 of the implant 10 facing the endplates 42, 46 when the implant 10 is in the fusion orientation. Thus, to maximize the gripping strength of the implant body 38 to the endplates, it is preferred that the upper surface 90 and lower surface 92 include the gripping surfaces 41, 43 and protrusions 40 thereof. Preferably, the gripping surfaces 41, 43 including the protrusions 40 are supported by sidewalls 60, and end walls 64 and 68 that span between superior and inferior endplates 42, 46 so that at least a portion of each wall 50 includes a portion of the upper and lower surfaces 90, 92. Beneficially, the compressive force transmitted from the endplates to the implant 10 is borne by each wall 50 in the generally vertical direction, and each wall is therefor utilized to provide support against the compressive load engaged with both endplates when in the fusion orientation. Such a configuration serves to distribute compression load from the patient's torso across the implant 10 to alleviate the risk of bone around the implant 10 subsiding and the adjacent vertebrae collapsing with the implant 10. As the implant 10 is rotated from the insertion orientation to the fusion orientation, the gripping surfaces 41, 43 are preferably uni-directional so that they resist counter-rotating once seated.

The endplates 42, 46 are cup-like and have a natural concavity in both the lateral direction and the anterior-posterior direction. Closely matching that concavity with the convexity of the fusion-oriented implant also serves to reduce the likelihood of bone subsidence and increase the purchase by the gripping surfaces 41, 43 into the endplates 42, 46. For this, a portion of the upper surface portion 90 and a portion of the lower surface portion 92 are each provided on each sidewall 60. The upper and lower surface portions 90, 92 have an arcuate profile, and, in the preferred embodiment, the arc is an arc of a circle such that the profile follows a predetermined radius of curvature.

Furthermore, it is believed that the size of the actual depression in the concave endplates 42, 46 is within range of 1.0 to 1.5 millimeters in the anterior-posterior direction. Therefore, the rise 98 of the upper and lower surface portions 90, 92 is preferably within this range (see FIG. 4).

As noted above, various sizes of implants 10 are preferably provided. As can be seen in FIG. 4, the implants 10 are generally specified by an anterior-posterior dimension 100 from the front wall 64 to rear wall 68, and by the overall height 102, exclusive of the gripping surfaces 41, 43. As the rise 98 is preferably kept in the noted range, the radius of curvature of the profile varies as the anterior-posterior dimension 100 varies over the range of implant sizes. It is also believed that the gripping surfaces 41, 43 should pierce or press into the endplates 42, 46 via the sharp protrusion peak 104 and approximately half-way down along a protrusion 40 and into the trough 106 on the upper and lower surfaces 90, 92 when secured in the fusion orientation.

Figure 36:
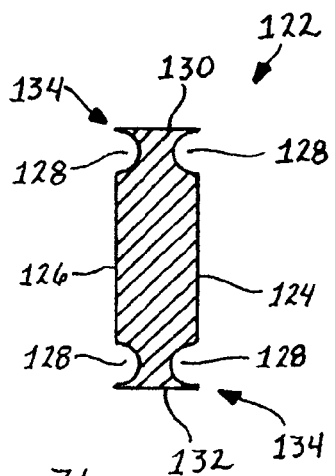
FIG. 36 is a cross-sectional view of the blade head of the scraping tool showing opposite sharp scraping ends thereon.

The surface contour of the endplates 42, 46 is, nevertheless, unpredictable and irregular from patient to patient, and from vertebrae to vertebrae. To improve the purchase and contact between the endplates 42, 46 and the implant 10, a preparatory tool for roughening or scraping an endplate is provided such as scraping tool 120, as is illustrated in FIGS. 34-36.

The scraping tool 120 includes a blade head 122 having an arcuate profile that generally matches the arcuate profile of the implant 10 that is to be utilized. As a number of different sized implants 10 are provided, a separate scraping tool 120 is provided for each. With specific reference to FIGS. 34 and 36, the blade head 122 includes relatively broad first and second sides 124, 126, each having a recess or gutter 128 immediately adjacent relatively narrow third and fourth sides 130, 132. In this manner, the gutters 128 and the third and fourth sides 130, 132 form cutting ends 134.

The scraping tool 120 is manually operated in the intervertebral space 30 to slightly shape the endplates 42, 46. To do so, the scraping tool 120 is rotated in the intervertebral space 30 so that the cutting ends 134 scrape or grind against the endplates, thereby removing or scoring and roughening a portion of the endplate. As the blade head 122 has a profile matching that of the implant 10, the scraping shapes the irregular surface of the endplates to have a profile to match that of the implant 10 to be received therein. By doing so, the endplates 42, 46 more closely match the contour of the implant 10 to be inserted, which helps reduce the likelihood of bone subsidence due to stress concentrations, and makes the implant 10 less likely to shift out of the vertebral space 30. Furthermore, the endplates 42, 46 sustain surface wounding that promotes blood and fluid flow necessary for bone ingrowth.

To perform the spinal fusion surgery, the initial step is resection of the surrounding tissue to provide access to the diseased or damaged portion of the spine 12. The natural spinal disc 16 is then removed, a procedure known as a discotomy. Once the disc 16 is removed, an assessment is made of the size of the intervertebral space 30.

Specifically, the assessment is made to determine the overall axial length 100 and height 102 for the implant 10. Because the actual implant 10 includes the gripping surfaces 40, insertion and removal of several different sizes of the implant 10 may cause significant damage to the endplates 42, 46.

Figure 39:
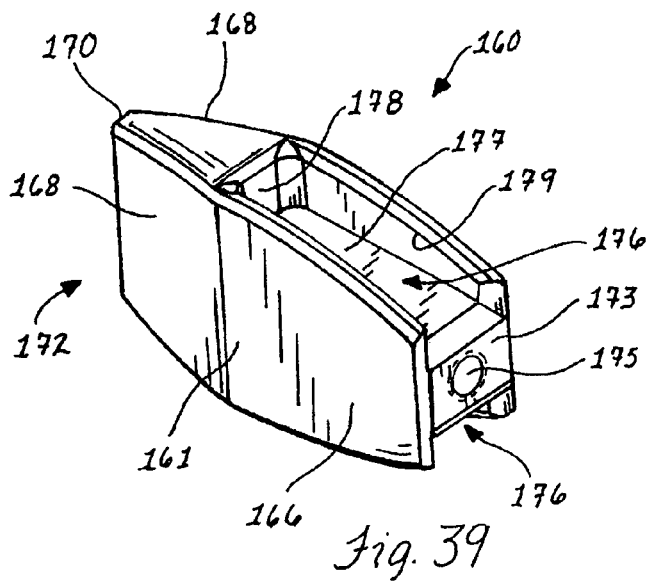
FIG. 39 is a perspective view of a trial spacer member for determining a proper size of VBR device.
Figure 40:
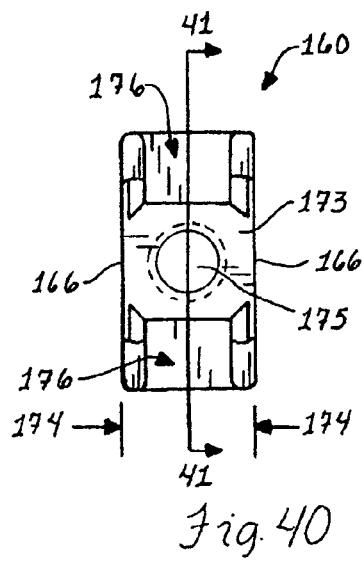
FIG. 40 is an end elevational view of an engagement end portion of the trial spacer member showing a connection end thereof.
Figure 41:
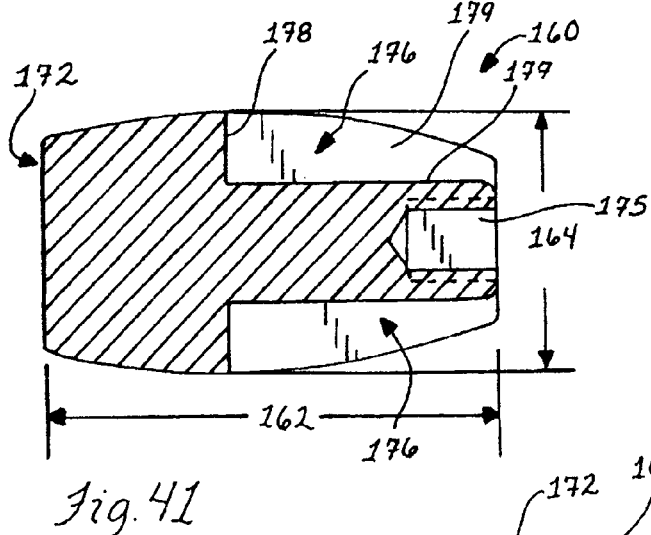
FIG. 41 is a cross-sectional view taken along line 41-41 of FIG. 40 showing tool connection structure thereof including a pair of receiver channels and a connection opening therebetween.
Figure 42:
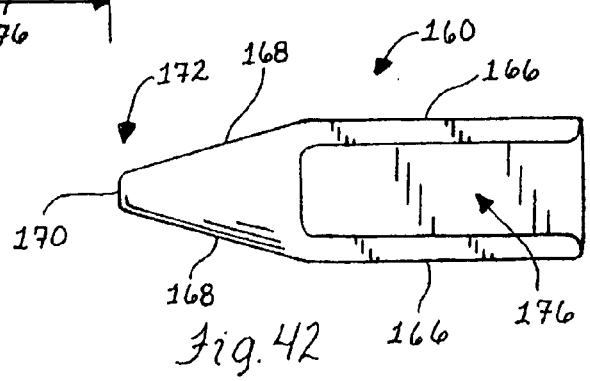
FIG. 42 is a plan view of the trial spacer member showing outer walls on either side of one of the receiver channels.

Instead, a series of trial spacer members 160 is provided, representatively depicted in FIGS. 39-40. Each trial spacer has an elongate, wedge shaped body 161 having an axial length 162 and height 164 corresponding to an implant 10 having no gripping surfaces 40. More specifically, the height 164 corresponds to height of the implant 10 troughs or valleys 106. In this manner, the trial spacer member 160 may be inserted into the intervetebral space 30 in the insertion orientation, rotated to the fusion orientation of the implant 10, counter-rotated back to the insertion orientation, and finally removed. This may be sequentially repeated until the proper sized trial spacer 160, and hence the proper sized implant 10, is determined.

As illustrated, the trial spacer member 160 has sides 166 corresponding to the sidewalls 60 of the implant 10. However, the sides 166 have leading portions 168 that taper inward toward a relatively small, narrow width front wall 170 at a leading insertion end 172. The front wall 170 and leading side portions 168 act wedge-like so that the trial spacer 160 cams the vertebrae 14 apart somewhat to ease entry of the trial spacer 160 into the intervertebral space 30. The trial spacer 160 is inserted by orienting the sides 166 generally with the endplates 42, 146 and inserting the trial spacer 160 between the endplates 42, 46. The trial spacer 160 is then rotated to the simulated fusion orientation of the implant 10. Again, this is repeated until the proper trial spacer 160 is determined. Once the proper trial spacer 160 has been determined based on its height 164 and length 162, the corresponding implant 10 is selected.

The proper trial spacer 160 may be temporarily left in the intervetebral space 30 as the implant 10 is inserted and rotated to the fusion orientation. As discussed above, it is preferred to perform spinal fusion surgery in the lumbar region of the spine 12 by inserting and fixedly securing a pair of implants 10. Accordingly, the trial spacer 160, located to one side of the spinal cord portion 22, may remain in the intervertebral space 30 in order to provide distraction to the adjacent vertebrae 14 as the first implant 10 is inserted and rotated. Once the first implant 10 is inserted and rotated to the fusion orientation, the trial spacer member 160 may be removed so that the second implant 10 replaces the trial spacer 160 in the intervertebral space 30. After the second implant 10 has been positioned in the fusion orientation, additional bone graft material may be provided in the remainder of the intervertebral space 30.

Alternatively, a spreading tool 180 may be utilized for distracting the vertebrae 14 adjacent the intervertebral space 30. Referring now to FIGS. 37 and 38, the spreading tool 180 includes a distraction head 182 having relatively broad first and second sides 184, 186 and relatively short or narrow third and forth sides 188, 190. The purpose of the spreading tool 180 principally is to distract the vertebrae 14 to allow the implant 10 to be inserted therein and rotated to the fusion orientation.

Accordingly, it is not necessary for the spreading tool 180 to have a convexity to match or approximate the concavity of the endplates 42, 46. To simplify the construction, and possibly reduce the number of sizes of spreading tools 180 needed, the narrow sides 188 and 190 are generally planar, and taper outwardly toward an insertion end 192. The spine 12 does not have a straight axis X throughout its length, instead having a varying curvature known as a lordosis. Each endplate 42, 46, although concave, has a general plane defined by lateral, anterior, and posterior-most points. The spinal lordosis results in the planes defined by adjacent vertebrae not being necessarily parallel. It is preferred that the angle Θ formed between the narrow sides 188 and 190 generally corresponds to the lordotic angle of the endplates of adjacent vertebrae 14. To distract the vertebrae 14, the spreader 180 is inserted with the broad sides 184, 186 facing the endplates 42, 46, and is then rotated so that the narrow sides 188, 190 contact the endplates 42, 46 and urge them apart.

As mentioned above, the implant 10 is inserted and rotated to the fusion orientation by an insertion tool or inserter 200. During insertion and rotation, the implant 10 and inserter 200 preferably are substantially rigidly coupled so that force directed through the inserter 200 does not cause the implant 10 to become dislodged from the inserter 200. In addition, a significant amount of torque is exerted when the implant 10 is rotated by the inserter 200 within the intervertebral space 30 to position the implant 10 in the fusion orientation. To this end, the inserter 200 and implant 10 have cooperating structure 201 for securing the implant 10 to the inserter 200.

Referring to FIGS. 3-12, the implant 10 includes a plurality of recesses for receiving portions of the inserter 200 therein. Specifically, the implant sidewalls 60 include elongate recesses or receiver channels 240 for receiving arm or prong portions 202 of the inserter 200, and the rear wall 68 includes a connection opening 250 for receiving an extension connection portion 220 of a longitudinal insertion member 264 of the inserter 200 therein.

The sidewall recesses 240 are generally rectangular recesses having a front wall 242, a generally flat base wall 244, and upper and lower walls 246, as shown in FIG. 5. Each inserter prong 202 has a generally matching configuration to the receiver channels 204 so that they are also generally rectangular and have an outer surface 204, a generally flat inner surface 206 that abuts flush against the base wall 244, a front wall 208 that abuts flush against the recess front wall 242, and upper and lower walls 210, 212 that abut flush against respective the upper and lower walls 246 of the sidewall receiver channel 240. In this manner, the prongs 202 are closely fit and slidingly received within the sidewall receiver channel 240. Such a close, mating fit maximizes surface area contact between the tool 200 and implant 10 to assist in distributing the forces endured by the tool engaging portions of the implant 10 when inserted into the intervertebral space 30 and when rotated therein.

As the implant 10 is directed into the intervetebral space 30, the sidewall receiver channels 240 and the exterior surface 204 of the implant 10 are oriented towards and facing the endplates 42, 46. To minimize or reduce the possibility of unnecessarily or undesirably damaging the endplates 60 by having the prongs 202 forced thereacross during insertion, the prongs 202 preferably are sized so that, with the prongs 202 fully received in the implant channel 240, the prong surfaces 204 are recessed from the respective surfaces 62 of the sidewalls 60.

The sidewall receiver channels 240 and the inserter prongs 202 are the principal means for rotating the implant 10 from the insertion orientation to the fusion orientation. For this, the inserter prongs 202 are a relatively strong, rigid material such as surgical grade stainless steel, as an example.

It is unfortunately expected that a surgeon will not always be able to direct the implant 10 directly in a proper insertion direction or rotate the implant 10 to the fusion orientation perfectly. In other words, it is expected that a surgeon may need to manipulate the implant 10 in some way other than preferred at some point after the implant insertion procedure has begun. For instance, the surgeon may realize the implant 10 is positioned in a skewed manner from the desired position, or may realize at the moment rotation begins that the resulting position of the implant 10 would be undesirable. Preferably, the connection between the implant 10 and the inserter 200 is not simply a friction fit, as such would likely make it very difficult to retain the implant 10 on the inserter 200 if such were necessary.

Therefore, the implant 10 is preferably easily held and secured to the inserter 200. For this purpose and as earlier mentioned, the implant rear wall, 68 has the connection opening 250 which receives the inserter extension member 220 therein to further secure the implant 10 to the inserter 200. In the preferred and illustrated form, the extension member 220 is a shaft 222 with a threaded end 224, and the connection opening 250 is internally threaded so as to threadingly receive the threaded end 224 of the extension member 220 to positively capture and hold the implant device 10 on the engagement end portion of the tool 200. As the extension member 220 is threaded into the connection opening 150, the connection end of the implant 10 is drawn into the space between the prongs 202 until the rear wall 68 of the implant 10 is engaged against an abutment surface 226 extending transversely between the prongs 202.

The inserter 200 accordingly has an elongate shaft 260 extending along longitudinal axis 260a having an engagement end portion 260b at the distal end at which the prongs 202 are generally rigidly secured, or with which they are integral. The elongate shaft 260 includes a central throughbore 262 in which the rod-like longitudinal member 264 is received, a distal portion 266 of which includes the extension member 220 having the threaded end 224. The longitudinal member 264 is permitted to rotate freely relative to the elongate shaft 260 and the throughbore 262. In addition, as the implant 10 slides in between the prongs 202, the longitudinal member 264 is permitted to linearly reciprocate freely within the throughbore 262.

In order to rotate the longitudinal member 264 to advance the threaded extension member 220 toward the implant 10 and in the threaded connection opening 150 thereof, a rotary actuator in the form of knob 270 is provided. More specifically, the elongate shaft 260 includes a handle portion 272 at a proximal end 274. The handle portion 272 includes a grip or T-bar 280 for gripping and manipulating the inserter 200 with the implant 10 secured thereto. The handle portion 272 includes an opening 276 within which the knob 270 is located. The opening 276 is larger than the knob 270 along the longitudinal axis of the elongate shaft 260 so that the knob 270 may move along the axis within the opening 276 a short distance.

However, the axial movement of the knob 270 is restricted by distal and proximal stop surfaces 276a, 276b bounding the opening 276 at either axially spaced end thereof. Specifically, the longitudinal member 264 threadably engages the implant 10 and, as it is threaded therein, contacts the stop, surface 276a. With continued rotation, the longitudinal member 264 is placed in tension as the knob 270 is against the stop surface 276a and the implant 10 is secured against the abutment surface 226 between the prongs 202. In addition, with counter-rotation of the knob 270 to release the longitudinal member 24 from the implant 10, the knob 270 shifts axially until contacting the stop surface 276b and, with continued rotation, forces the threadably received implant 10 away from the prongs 202 and from the longitudinal member 264 itself.

Once the implant 10 is secured to the tool engagement end portion, it can be inserted into the intervertebral space 30 in the insertion orientation, and then rotated to the fusion orientation. The knob 270 may then be counter-rotated so that the threaded end 224 of the longitudinal member 264 is released from the connection opening 250. The inserter 200 may then be withdrawn so that the prongs 202 release from the sidewall recesses 240 and the inserter 200 is removed from the surgical site.

As depicted, the trial spacer member 160 may also be connected with the inserter 200 in the same manner as the implant 10. However, for ease of insertion, the trial spacer member 160 is provided with a width 174 smaller than width 108 of the implant 10 (see FIG. 5). For this purpose, the trial spacer 160 has upper and lower receiver channels 176 corresponding to the sidewall receiver channels 240 of the implant 10. The prongs 202 of the inserter 200 are received within the upper and lower receiver channels 176 so that the inserter interior surface 206, front wall 208, and upper and lower walls 210, 212 are received respectively flush within and against a trial spacer base surface 177, a front wall 178, and side outer walls 179 defining each of the receiver channels 176. The trial spacer 160 further includes a rear wall 173 including an internally threaded connection opening 175 for receiving the threaded end 224 of the longitudinal member 264 and corresponding to the connection opening 250 of the implant 10. As such, the threaded end 224 threads into the trial spacer rear wall 173 to draw trial spacer member 160 towards the abutment portion 226 between the prongs 202. At the same time, the prongs 202 are received in the upper and lower receiver channels 176.

As can be seen, the inserter tool 200 is utilized with the trial spacer 160 and the implant 10. However, the tool 200 is utilized by inserting the implant 10 in the insertion orientation with the prongs 202 of the inserter respectively aligned with the general axis X of the spine 12 so that the prongs 202 are oriented so as to face the endplates during insertion and when in the insertion orientation. In contrast, the trial spacer 160 is inserted with the prongs 202 received in the receiver channels 176 so the prongs 202 are oriented in a lateral direction. The implant 10 in the orientation is then rotated approximately ninety degrees to the fusion or implantation orientation, at which point the gripping surfaces 41, 43 provide a significant impediement to removal of the implant 10, as well as the inserter tool 200 unless the tool 200 is deliberately disengaged. The trial spacer 160, on the other hand, is rotated to the simulated implantation orientation, and then is rotated back to the insertion orientation for removal.

With reference to FIG. 1, the T-bar 280 of the tool 200 is seen in a first, generally vertical orientation when the implant 10 is in the insertion orientation. In FIG. 2, the T-bar 280 is seen in a generally horizontal orientation when the implant 10 is in the implantation orientation. For the trial spacer 160, the orientations would be reversed such that the T-bar 280 is in a generally horizontal orientation during insertion and in the insertion orientation, as well as would be in a generally vertical orientation when rotated ninety degrees to the simulated implantation orientation.

Accordingly, a surgeon utilizing the inserter 200 with the T-bar 280 may easily determine what device, either the implant 10 or the trial spacer 160, is located in the vertebral space. As discussed, the trial spacer 160 may be utilized as a spacer to distract the vertebrae. This allows another inserter 200 to inserting an implant 10. Because the secured implant 10 and the trial spacer 160 in the simulated implantation orientation cooperate with the inserter 200 so that the inserter 200 is in a different orientation depending on the device, the surgeon not only is able to utilize a single, universal instrument, but can also recognize what type of device is connected to the instrument 200 when the device is located within the intervertebral space 30.

The implant 10 is intended to be permanent and to provide support equivalent to the support properties of the natural disc that was removed, though without providing the range of movement. In contrast, the trial spacer member 160 is only intended to examine the size of the intervertebral space 30 so the proper sized implant 10 may be selected. In addition, the trial spacer 160 may be used as a distractor for opening the vertebral space 30 for receiving the implant 10. Accordingly, the trial spacer member 160 is smaller in width to force the vertebrae apart, whereas the implant 10 is designed to be inserted into a distracted space 30. Moreover, the trial spacer 160 is to be removed during the procedure to allow an implant 10 to be inserted in the space 30. For this reason, the trial spacer 160 is provided that is removable, and therefore has no gripping surfaces 41, 43 that would hinder or prevent removal, as well as may damage the endplates.

The scraping tool 120 and the spreading tool 180 preferably connect to a tool or the like for allowing a surgeon to manipulate them. As illustrated in FIGS. 34, 35, 37 and 38, the scraping tool 120 and spreading tool 180 have respective integrally formed shafts 136, 194, and tool connection ends 138, 196. A tool (not shown) may be attached to the tool connection ends 138, 196 for manipulating and inserting the scraping tool 120 and spreading tool 180. For the scraping tool 120, the tool would be used to allow a surgeon to rotate the scraping tool 120 within the intervertebral space 30 so that the scraping ends 134 roughen the surface to stimulate blood and fluid flow and so that the scraping ends 134 having a profile substantially identical to that of the implant shapes the irregular endplate to have a profile substantially identical to that of the implant 10. For the spreading tool 180, the tool connected to the connection end 196 allows the spreading tool 180 to be forced between the adjacent vertebra, and then be rotated to distract the vertebrae to their inherent lordotic angle. However, it is preferred that the scraper blade head 122 and spreader distraction head 182 are equipped with a connecting structure such as that described above for the implant 10 and trial spacer members 160. In this manner, the inserter 200 may be used with each component of the system described herein.

Referring to now to FIGS. 13-21, an insertion tool 300 and implant device 350 are depicted having an alternative configuration for connecting with each other. The inserter 300 and implant 350 form an insert-and-turn, or bayonet connection. In contrast to the inserter 200, the preferred form of the insertion tool 300 includes only a single component requiring no moving parts or components.

The insertion tool or inserter 300 has an elongate rod-like body portion 302 and a handle (not shown) for manipulating and inserting the implant 350 in the insertion orientation and then rotating the implant 350 to the fusion orientation, as described above. The body portion 302 includes a pair of prongs 304 extending from a distal end 306 of the body 302. The prongs 304 are received by recesses or receiver channels 352 formed in sidewalls 354 of the implant 350. The channels 352 extend a predetermined distance 355 from a trailing, connection end 356 of the implant body 398 toward a leading insertion end 358. The prongs 304 have arcuate inwardly facing surfaces 308 that engage flush against an arcuate base wall 360 in the recesses 352 of the implant 350.

The prongs 304 are generally L-shaped. That is, the prongs 304 have a longitudinal portion 320 extending from the body portion 302 for an extent approximately equal to the length 355 of the sidewall receiver channels 352. At a distal end 322 of the prongs 304, a grip head portion 324 extends from the longitudinal portion 320. The grip head portions 324 are enlarged in a transverse direction with respect to the longitudinal portions 320. For the respective prongs 304, each has a grip head portion 324, and both grip head portions 324 extend in the same clockwise or counter-clockwise direction. The rotational direction in which the grip head portions 324 extend determines the rotational direction for shifting the implant 350 from the insertion orientation to the fusion configuration.

Accordingly, for the illustrated form of FIGS. 15 and 16, the grip head portions 324 of the inserter 300 would be rotated clockwise. More specifically, a surgeon manipulating the inserter 300 would view the inserter 300 and implant 350 from a proximal end 323 to the distal end 306. In this frame of reference, the grip head 324 are oriented to extend from their respective prong arms 304 in a clockwise fashion.

The implant 350 and inserter 300 are attached by first sliding the inserter prongs 304 into the receiver channels 352 of the implant 350 with the complementary arcuate surfaces 308, 360 engaging and sliding against each other. The inserter 300 and implant 350 are secured together by a short amount of relative rotation therebetween.

Figure 18:
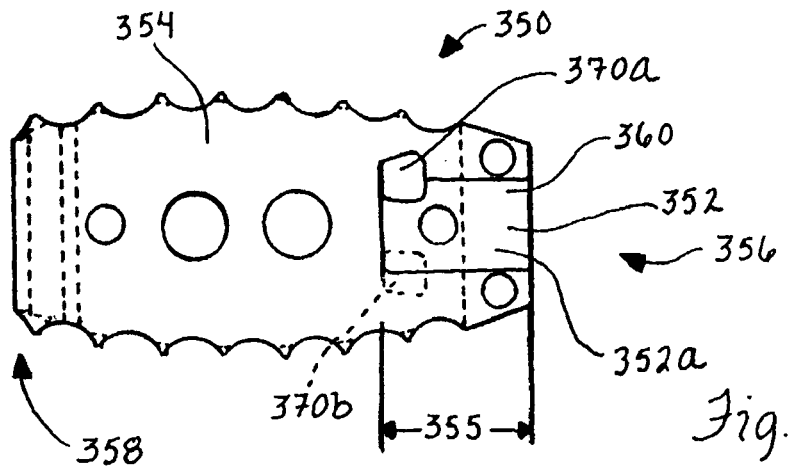
FIG. 18 is a side elevational view of the VBR device of FIG. 13 showing one side of a body of the VBR device including one of the receiver channels having a transverse notch opening for one of the prong grip heads of the tool.
Figure 19:
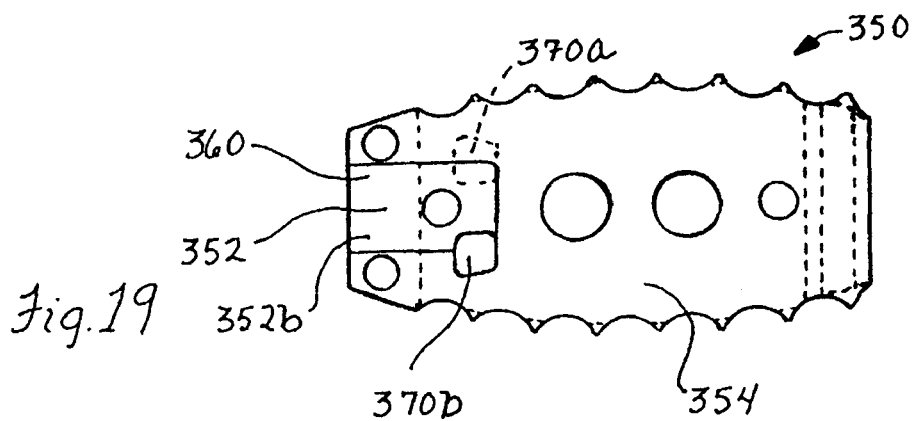
FIG. 19 is a side elevational view of the VBR device of FIG. 13 showing an opposite side of the VBR device including the other receiver channel having another transverse opening for the other prong grip head.
Figure 20:
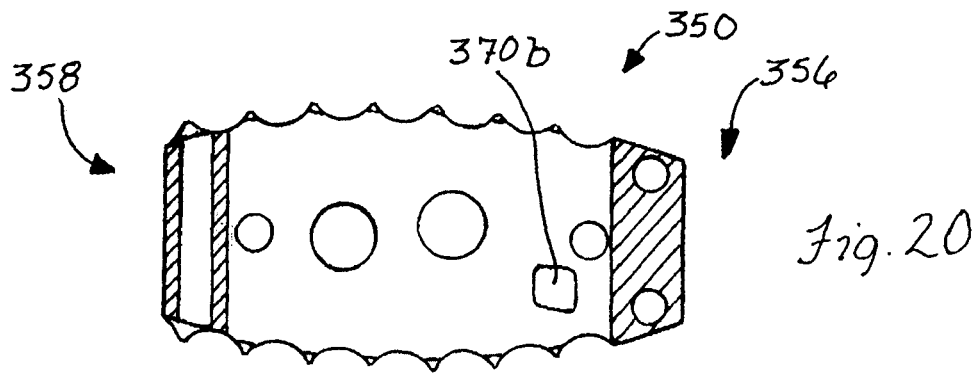
FIG. 20 is a cross-sectional view taken along line 20-20 of FIG. 17 showing the location of one of the grip head openings relative to the bores and apertures of the VBR device body.

More specifically and referring to FIG. 18, a first transverse notch opening 370a is positioned in the implant 350 at least partly beyond and partly coincident with the first receiver channel 352a in the direction of rotation. Additionally, the first notch opening 370a extends transversely relative to the longitudinally or axially extending receiver channel 352a in the implant body 398. Referring to FIG. 19, a second transverse notch opening 370b is formed in the same manner with the second receiver channel 352b. The notches 370a, 370b are formed so as to extend in the direction of rotation from the receiver channel 352a, 352b. With this configuration, prongs 304 may be rotated once inserted into the receiver channels 352a, 352b so that respective the grip head portions 324 are received into the first and second notch openings 370a, 370b. In the preferred form of this connection, the relative rotation required between the implant 350 and the inserter 300 is approximately 10 degrees.

As can be seen, the longitudinal member is rotated axially in a first direction so that so that the grip heads 324 are shifted into the notch openings 370a, 370b. The implant is inserted, and then is rotated within the intervertebral space to the implantation orientation by axially rotating the longitudinal member and the implant in the same, first direction as for shifting the grip heads 324 and notch heads into engagement. To remove the inserter, it is simply counter-rotated in a second direction. In this manner, rotation of the implant 10 in the intervertebral space 30 to shift the implant to the implantation orientation is in the same direction as securing, thereby minimizing the likelihood of the inserter and implant becoming unintentionally disengaged. However, the directions could also be reversed.

In this manner, the implant 350 and inserter 300 are substantially locked together against axial separation and ready for the insertion procedure. Once the implant 350 has been located within the intervertebral space 30 and rotated approximately 90 degrees to the fusion configuration, the inserter 300 need only be counter-rotated (or, rotated in the opposite direction as the direction in which the implant 350 was rotated to shift to the fusion orientation) the same 10 degrees to release the inserter 300 from the implant 350.

Referring now to FIGS. 22-26, the implant 500 for being inserted in the cervical portion of the spine 12 is illustrated. The vertebrae 14 in the cervical region are significantly smaller than the vertebrae 14 in the lumbar region. In addition, the cervical vertebrae are not as complicated to reach from the anterior side 18. For these reasons, an intervertebral space 30 on the cervical portion may be fused with a single implant 500 inserted from the anterior side 18.

In addition, the cervical vertebrae 14 are slightly open in the anterior direction due to the lordosis of the vertebrae 14 and, therefore, allow relatively easy insertion of the implant 500 between the vertebrae 14. Accordingly, the implant 500 is not rotated to a fusion orientation, instead simply being implanted directly therein with the fusion orientation.

The implant 500 includes a body 538 having substantially annular outer wall 502 having a contoured outer surface 604 and upper and lower surfaces 520, 522 that, preferably, including gripping surfaces 41, 43 including protrusions 40 for engaging and piercing the endplates. Because of the relatively small size of the implant body 538 for the cervical region, the implant body 538 further includes a central web wall 504 extending in the fore and aft or anterior-posterior direction to span from a leading, insertion end 506 to a trailing, connection end 508, thereby providing additional strength and rigidity to the implant 500.

Throughopenings 507 for allowing fluid flow through the implant 500, as described above, are formed in the outer wall 502. The openings 507 lead to the cavities 509 in which packed bone graft material is disposed. In this manner, the implant 500 encourages and promotes bone ingrowth between the adjacent vertebrae 14, in the intervertebral space 30, and through the implant 500.

Radiographic markers or rod members 80 also provide additional support to the implant 500. The markers are positioned, for example, at diametrically opposite corners 510 of the implant 500 in a generally vertical orientation when in the implant orientation so as to provide additional compression strength to the implant 500.

The implant 500 includes the above-described convex arcuate profile. The outer wall 502 and the central web wall 504 have an arcuate profile in the anterior-posterior, or fore and aft, direction such that the rise of the profile is approximately 1-1.5 millimeters. The arcuate convex profile closely follows the arcuate concave surface of the endplate. This close mating allows compression force through the spinal column 12 to be distributed across the implant 500 and across the endplate, thereby reducing or minimizing the likelihood of subsidence of the vertebrae with the implant 500 due to high stress concentrations.

The outer wall 502 and web 504 further are provided with upper and lower gripping surfaces 41, 43 for contacting and engaging the endplates 42, 46. The gripping surfaces 41, 43 are located on a upper surface 520 and a lower surface 522 of the implant 500. The gripping surfaces 41, 43 preferably also include the protrusions 40 having peaks 104 and troughs 106 that are received in the endplates approximately half peaks 104 towards the troughs 106 for fixedly securing with the endplates. The protrusions 40 are preferably uni-directional.

Figure 27:
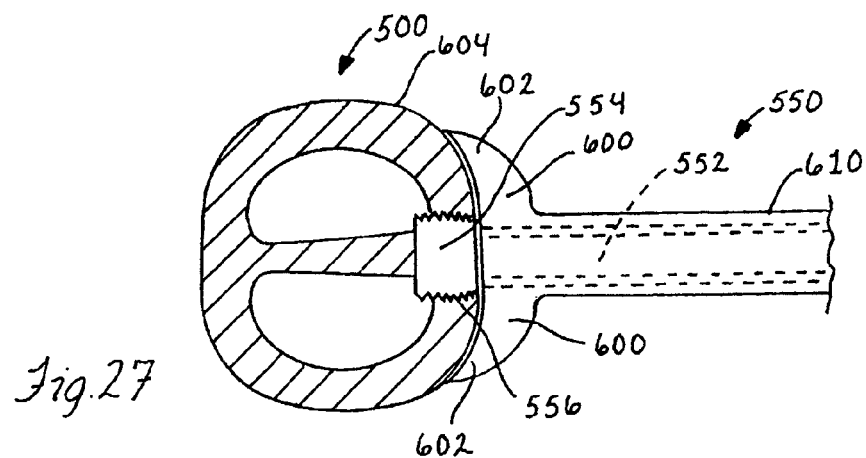
FIG. 27 is a plan view of an inserter tool for implanting the VBR device of FIG. 22 showing cooperating threaded connection structure for interconnecting the tool and the VBR device.

In order to insert the implant 500 into the intervertebral space 30, the implant 500 may be connected to an insertion tool 550, as illustrated in FIG. 27. In its simplest form, the inserter tool 550 includes a central member 552 with a threaded extension 554 which is threadably received in a connection opening 556 formed in the connection end 508. In order to strengthen the implant 500 in the region surrounding the connection opening 556, the central wall 504 is thickened in the region proximate to the connection opening 556, as can be seen in FIG. 27.

In addition, the insertion tool 550 may be provided with a brace 600 in the form of a pair of arcuate arms 602 extending laterally from the central member 552 to generally form a C-shape. The arms 602 may be placed against the exterior surface 604 of the implant body 538 about the connection opening 556 and tightly secured thereagainst by drawing the implant 500 against the arms 602 with the threaded central member 552 received in the connection opening 556. Accordingly, the brace 600 including the arms 602 is formed on a body 610 which cooperates with the central member 552 in the same manner as the elongate shaft 260 and longitudinal member 264 for the above-described inserter 200.

Figure 33:
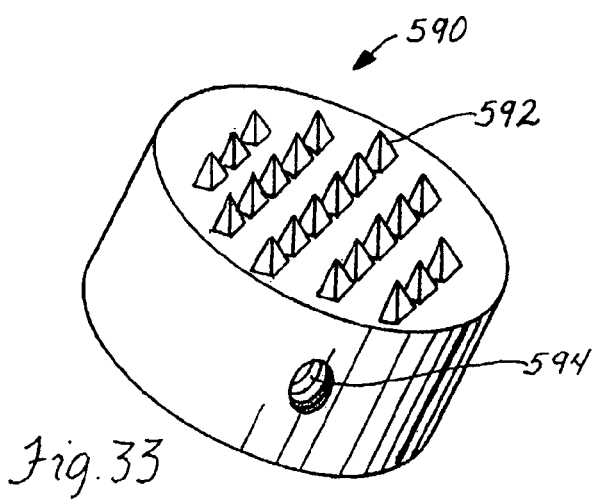
FIG. 33 is a perspective view of a scraping member showing a rasping surface for preparing the facing endplates of adjacent vertebrae for receiving a VBR device.

In contrast to the implant 10 for the lumbar region, it is preferred not to use the described scraping tool 120 for roughening and wounding the endplates 42, 46. Instead, a rasp scraping member 590 may be used, as illustrated in FIG. 33. The rasp 590 has a disc-shaped body 591 with one or more roughened faces or rasping surfaces 592 for scraping and wounding the endplates 42, 46, as described above, and inducing fluid and blood flow into the intervertebral space 30, which promotes bone ingrowth. The rasp 590 includes a connection opening 594 located on one side similar to the connection opening 556 of the implant 500, and the rasp 590 may be manipulated and handled with the same inserter tool 550. Alternatively, a tool (not shown) having a threaded member for being received in the connection opening 556 and having pegs or bosses cooperating with recesses in the rasp 590, or vice versa. As a further alternative, a collet ring (not shown) having a circular rim may be used to scrape at the endplates 42, 46 to induce blood and fluid flow.

Referring now to FIGS. 28-32, an implant 700 for the cervical region and an inserter tool 750 for cooperating with the implant 700 are illustrated. Cooperating connecting structure between the implant and the inserter is provided in the form of a keyhole and key structure 703.

Figure 31:
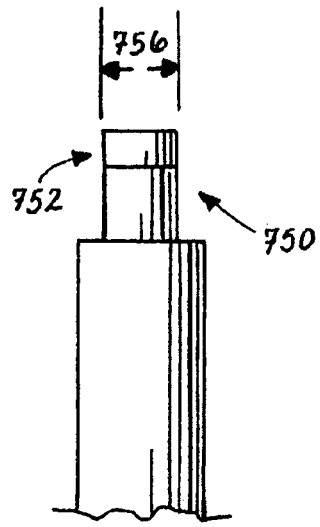
FIG. 31 is a fragmentary side elevational view of an inserter tool showing an end engagement portion for cooperating with the connection end of the VBR device of FIGS. 28-30.
Figure 32:
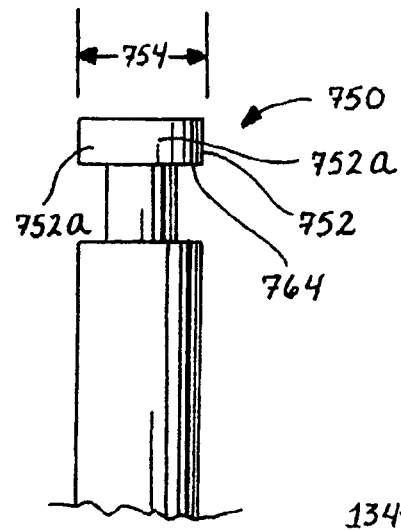
FIG. 32 is a fragmentary side elevational view of the inserter tool rotated ninety degrees from the view of FIG. 31 to show the enlarged grip head of the end engagement portion.

The implant 700 includes a body 701 in which an asymmetrical connection opening 702 is provided as the key-hole for connecting with the inserter tool 750. The inserter tool 750 has an asymmetrical extension 752 for the mating key for being inserted into the connection opening 702. More particularly, the extension 752 includes a shaft portion 760 and an enlarged head portion 762 at the free end of the extension 752. As shown in FIG. 31, the diameter of the shaft 760 is the same as the minor dimension of the head 762. On the other hand, it can be seen in FIG. 32 that the major dimension of the head 762 is larger than the shaft 760 diameter as the head 762 extends beyond the shaft 760 at both sides thereof with corresponding shoulder surfaces 764 formed with head portion.

The extension 752 is axially received within the opening 702 so that the enlarged head 762 is received therein with the shoulder surfaces 764 extending in a generally vertical direction. The extension 752 is then axially rotated within the opening 702 so that the shoulder surfaces 764 of the enlarged head 762 are engaged with the wall 708 formed in the opening 702 and facing anteriorly, and extension wings 752a extending outward from the shaft 760 are rotated to lateral portions 711 of the inner portion 707 of the opening 702. Therefore, the inserter 750 is cooperatively engaged with the implant 700 for implantation.

Figures 28, 29:
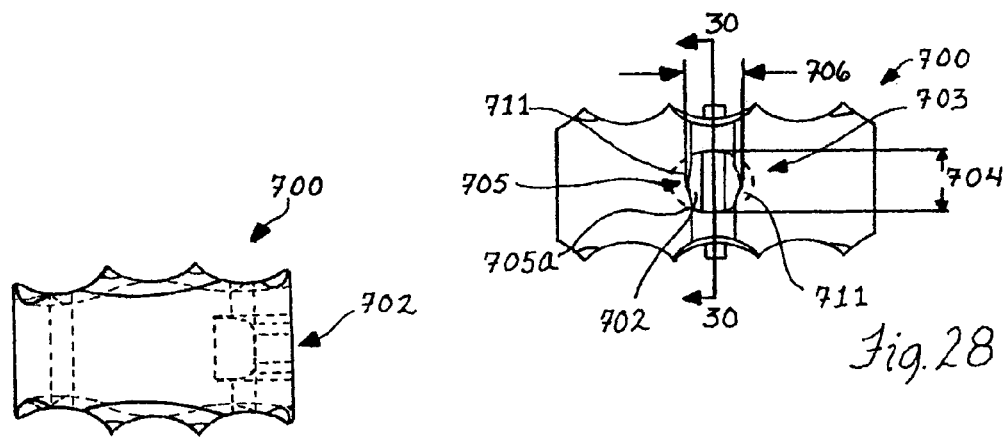
FIG. 28 is a front elevational view of a VBR device similar to FIGS. 22-26 showing alternative tool connection structure.
FIG. 29 is a side elevational view of the VBR device of FIG. 28 showing the tool connection structure including an inner enlarged opening portion in phantom.

As can be seen in FIG. 28, the implant body 701 has the key-hole connection opening 702 for receiving the extension 752 in a secured manner. The connection opening 702 has a first portion 703 presented in the posterior direction 20 having a major dimension 704 for receiving the major dimension of the head 762 therethrough and having a minor dimension 706 for receiving the minor dimension of the head 762 and the shaft portion 760 therethrough. The major dimension 704 generally extends in a vertical direction, and the minor dimension 706 generally extends in a horizontal or lateral direction. A central portion 705 of each lateral side 705a of the first portion 703 is generally circular in shape for receiving the shaft 760 therein. When the extension 752 is inserted, the central portion 705 is shaped to permit the shaft 760 to rotate therewithin.

Figure 30:
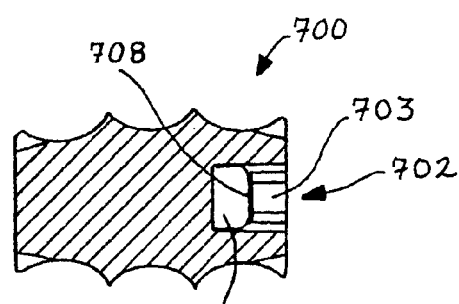
FIG. 30 is a cross-sectional view taken along line 30-30 of FIG. 28 showing the tool connection structure including the enlarged opening portion.

Referring to FIG. 30, the extension 752 is inserted into the first portion 703 of the connection opening 702 and then into a second portion 707. The second portion 707 is dimensioned to be greater than the first portion 703 in the lateral direction, thereby forming a wall 708 within the opening 702, the wall 708 facing the anterior direction. The inserted extension 752 and the head 762 may be rotated within the opening 702 so that the major dimension of the head 762 is no longer aligned with the major dimension 704 of the opening 702. In this manner, the extension 752 may be inserted into the connection opening 702 with the major dimension of the head 762 aligned with the major dimension 704 of the connection opening 702 and the minor dimension of the shaft 706 and head 762 aligned with the minor dimension 703. The head 762 passes through the first portion 703 to the second portion 707 and, to secure the implant 700 and inserter 750 together, the inserter 750 is rotated approximately ninety degrees so that the major dimension 754 of the head 762 is rotated so that it is not aligned with the major dimension 704 of the opening 702. Accordingly, the major dimension 754 of the head 752 is in an interference position with the wall 708, and the extension 752 is able to retain the implant 700 thereon. In this configuration, the inserter 750 may be used to insert the implant 700 into the intervertebral space 30.

Though the inserter tool 750 and connection opening 702 are illustrated with reference to an implant 700 for the cervical region, the described structures may also be utilized on an implant for the lumbar region where the implant is rotated from an insertion orientation to a fusion orientation. In such a case, a supper or other constraint would simply be formed or placed at some point in the connection opening 702 to prevent rotation beyond the supper.

It should be noted that each implant described herein may be extracted or removed from its intervertebral site by using a tool that attaches to the holes located on the sides of the implant. In addition, extraction may achieved with a number of the embodiments by using the same inserter tool, and simply reversing the steps.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A system for implanting an implant device in an intervertebral space between adjacent vertebrae, the system including:
an implant device for implantation in the intervertebral space between adjacent vertebrae, the implant device having vertebral facing surfaces including gripping protrusions extending therefrom to engage and grip the corresponding vertebra;
a trial device for insertion into the intervertebral space between adjacent vertebrae for determining proper sizing of the implant device to be removed therefrom after the sizing determination, the trial device having outer surfaces that are free of gripping protrusions to allow for the trial device to be removed from the intervertebral space without damaging the vertebrae;
a preparatory device for preparing the adjacent vertebrae for receiving the implant device in the intervertebral space therebetween; and
a tool configured to be directly and rigidly secured to each of the implant device, the trial device, and the preparatory device for inserting any one of the implant device, the trial device and the preparatory device secured thereto into the intervertebral space,
wherein a tool engagement end portion of each of the implant device, the trial device, and the preparatory device has the same tool connecting structure, and the tool includes a connection portion configured to be directly and rigidly secured to the tool connecting structure of the tool engagement portion of each of the implant device, the trial device, and the preparatory device to provide a common connection interface directly between the tool and the implant device, the trial device, and the preparatory device to allow the same tool to hold and insert each of the implant device, the trial device, and the preparatory device into the intervertebral space and to remove the trial device and the preparatory device therefrom.

2. The system of claim 1 wherein the implant device comprises a plurality of differently sized implant devices and the trial device comprises a plurality of differently sized trial devices, with each of the differently sized trial devices having a size that generally corresponds to one of the differently sized implant devices.

3. The system of claim 1 wherein the implant device comprises a plurality of differently sized implant devices, with each of the implant devices having an implant body including vertebral engaging surfaces having gripping protrusions extending therefrom to engage and grip the vertebral surfaces with the implant device inserted in the intervertebral space, and the trial device comprises a plurality of differently sized trial devices, with each of the differently sized trial devices having a size that generally corresponds to one of the differently sized implant devices.

4. The system of claim 1 wherein the trial device includes upper and lower surfaces and a trailing end, and respective channels formed in the upper and lower surfaces and a threaded opening at the trailing end, and the tool includes a pair of spaced prongs configured to be received by the channels and a threaded portion configured to be received by the threaded opening.

5. The system of claim 1 wherein the preparatory device includes a shaft with a tool engagement end comprising opposite planar surfaces and a trailing end having a threaded opening therein, and the tool includes a pair of spaced prongs configured to be received by the opposite planar surfaces and a threaded portion configured to be received by the threaded opening.

6. The system of claim 1 wherein the implant device includes opposite side surfaces and a trailing end, and respective channels formed in the opposite side surfaces and a threaded opening at the trailing end thereof, the preparatory device includes a shaft with a tool engagement end comprising opposite planar surfaces and a trailing end, and a threaded opening at the trailing end, and the tool includes a pair of spaced prongs configured to be received by both the implant device channels and the preparatory device planar surfaces, and a rotatable shaft having a distal threaded portion configured to be threadingly received by both the implant device threaded opening and the preparatory device threaded opening.

7. The system of claim 1 wherein the preparatory device includes a surface configured for altering the surface of a vertebra.

8. The system of claim 7 wherein the preparatory device surface comprises a roughened surface for scraping the surface of a vertebra.

9. The system of claim 7 wherein the preparatory device surface comprises a cutting surface for contouring the surface of a vertebra.

10. The system of claim 1 wherein the implant device includes opposite side surfaces and a trailing end, and respective, generally L-shaped channels formed in the opposite side surfaces, each of the L-shaped channels having a first portion extending longitudinally from the trailing end and second portion extending generally perpendicular to the first portion, and the tool includes a pair of spaced L-shaped prongs, each of the L-shaped prongs having a first portion extending longitudinally from the tool and a second portion extending generally perpendicular to the first portion, with each of the L-shaped prongs configured to be received by the first portion of the L-shaped channels and to engage the second portion of the L-shaped channels upon rotation of the tool in a first direction.

11. A system for implanting an implant device in an intervertebral space between adjacent vertebrae, the system including:
an implant device for implantation in the intervertebral space between adjacent vertebrae, the implant device having vertebral facing surfaces including gripping protrusions extending therefrom to engage and grip the corresponding vertebra;
a trial device for insertion into the intervertebral space between adjacent vertebrae for determining proper sizing of the implant device to be removed therefrom after the sizing determination, the trial device having outer surfaces that are free of gripping protrusions to allow for the trial device to be removed from the intervertebral space without damaging the vertebrae;
a preparatory device for preparing the adjacent vertebrae for receiving the implant device in the intervertebral space therebetween; and
a tool configured to be secured to each of the implant device, the trial device, and the preparatory device for inserting any one of the implant device, the trial device and the preparatory device secured thereto into the intervertebral space,
wherein a tool engagement end portion of each of the implant device, device, and the preparatory device has the same tool connecting structure, and the tool includes a connection portion configured to be secured to the tool connecting structure of the tool engagement portion of each of the implant device, the trial device, and the preparatory device to provide a common connection interface between the tool and the implant device, the trial device, and the preparatory device to allow the same tool to hold and insert each of the implant device, the trial device, and the preparatory device into the intervertebral space and to remove the trial device and the preparatory device therefrom, and wherein the implant device includes opposite side surfaces and a trailing end, and the implant device tool engagement end portion includes respective channels formed in the opposite side surfaces and a threaded opening at the trailing end, the trial device includes upper and lower surfaces and a trailing end, and the trial device tool engagement end portion includes respective channels formed in the upper and lower surfaces and a threaded opening at the trailing end, and the tool connecting structure of the tool includes a pair of spaced prongs configured to be received by both the implant device channels and the trial device channels, and a rotatable shaft having a distal threaded portion configured to be threadingly received by both the implant device threaded opening and the trial device threaded opening.

* * * * *

UNITED STATES PATENT AND TRADEMARK OFFICE
CERTIFICATE OF CORRECTION

| | | |
|---|---|---|
| PATENT NO. | : 8,029,512 B2 | Page 1 of 1 |
| APPLICATION NO. | : 11/259403 | |
| DATED | : October 4, 2011 | |
| INVENTOR(S) | : Adam Paltzer | |

It is certified that error appears in the above-identified patent and that said Letters Patent is hereby corrected as shown below:

IN THE CLAIMS:

Claim 11, Column 18, Line 66, after "implant device," insert -- the trial --.

Signed and Sealed this
Second Day of October, 2012

David J. Kappos
*Director of the United States Patent and Trademark Office*